(12) United States Patent
Schoenberger et al.

(10) Patent No.: US 11,673,855 B2
(45) Date of Patent: *Jun. 13, 2023

(54) VOLTAGE GATED SODIUM CHANNEL IMAGING AGENTS

(71) Applicant: The General Hospital Corporation, Boston, MA (US)

(72) Inventors: Matthias Schoenberger, Charlestown, MA (US); Jacob Hooker, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/395,356

(22) Filed: Aug. 5, 2021

(65) Prior Publication Data

US 2022/0267254 A1 Aug. 25, 2022

Related U.S. Application Data

(63) Continuation of application No. 16/477,257, filed as application No. PCT/US2018/013287 on Jan. 11, 2018, now Pat. No. 11,117,858.

(60) Provisional application No. 62/445,045, filed on Jan. 11, 2017.

(51) Int. Cl.
    *C07C 231/12* (2006.01)
    *C07C 237/04* (2006.01)
    *A61K 51/04* (2006.01)

(52) U.S. Cl.
    CPC .......... *C07C 231/12* (2013.01); *C07C 237/04* (2013.01); *A61K 51/04* (2013.01); *C07B 2200/05* (2013.01)

(58) Field of Classification Search
    CPC ..... C07C 231/12; C07C 237/04; A61K 51/04; C07B 2200/05
    USPC ....................................................... 514/617
    See application file for complete search history.

(56) References Cited

U.S. PATENT DOCUMENTS

| 3,876,700 | A  | 4/1975  | Ross et al. |
| 7,449,581 | B2 | 11/2008 | Chen et al. |
| 11,117,858 | B2 | 9/2021 | Schoenberger et al. |
| 2005/0249662 | A1 | 11/2005 | Dolle |
| 2013/0072471 | A1 | 3/2013 | Marron et al. |

FOREIGN PATENT DOCUMENTS

WO   WO 2007/120647   10/2007

OTHER PUBLICATIONS

"Pubchem CID 4712629" Create Date: Sep. 16, 2005 (Sep. 6, 2005) Date Accessed: Jun. 4, 2018 (Jun. 4, 2018); p. 4.
Bean, "The action potential in mammalian central neurons," Nat. Rev. Neurosci., Jun. 2007, 8:451-465.
Collinsworth et al., "The Clinical Pharmacology of Lidocaine as an Antiarrhythymic Drug," Circulation, Dec. 1974, 50:1217-1230.
DeBlasi et al., "Calculating receptor number from binding experiments using same compound as radioligand and competitor," Trends Pharmacol. Sci., Jun. 1989, 10(6):227-229.
Gellens et al., "Primary structure and functional expression of the human cardiac tetrodotoxin-insensitive voltage-dependent sodium channel," Proc. Natl. Acad. Sci. USA, Jan. 1992, 89:554-558.
Hesse et al., "Dilated cardiomyopathy is associated with reduced expression of the cardiac sodium channel Scn5a," Cardiovasc. Res., 2007, 75:498-509.
Japp et al., "The Diagnosis and Evaluation of Dilated Cardiomyopathy," J. Am Coll. Cardiol., Jun. 2016, 67(25):2996-3010.
Kwong et al. "Voltage-gated sodium channels," Curr. Opin. Pharmacol., Jun. 2015, 22:131-139.
Lee et al., "Blood Volume in the Rat," J. Nucl. Med., Jan. 1985, 26:72-76.
PCT International Preliminary Report on Patentability in International Appln. No. PCT/US2018/013287, dated Jul. 25, 2019, 7 pages.
PCT International Search Report and Written Opinion in International Appln. No. PCT/US2018/013287, dated Jun. 21, 2018, 14 pages.

*Primary Examiner* — Kristin A Vajda
(74) *Attorney, Agent, or Firm* — Fish & Richardson P.C.

(57) ABSTRACT

Provided herein are radiolabeled compounds useful for minimally invasive imaging techniques. An exemplary radiolabeled compound provided herein is useful as a radiotracer for position emission tomography imaging of voltage gated sodium channels. Methods for prepared unlabeled and labeled compounds, and diagnostic methods using the compounds are also provided.

20 Claims, 12 Drawing Sheets

VOLTAGE GATED SODIUM CHANNEL IMAGING AGENTS

CROSS-REFERENCE TO RELATED APPLICATIONS

This application is a continuation of U.S. patent application Ser. No. 16/477,257, filed Jul. 11, 2019, which is a national stage application under 35 U.S.C. § 371 of International Application No. PCT/US2018/013287, filed on Jan. 11, 2018, which claims the benefit of U.S. Provisional Application Ser. No. 62/445,045, filed Jan. 11, 2017, the disclosure of which is incorporated herein by reference in its entirety.

FEDERALLY SPONSORED RESEARCH OR DEVELOPMENT

This invention was made with Government support under Grant Nos. HL116848, HL127240, AG043822, TR001082, S10RR017208, and S10RR023452 awarded by the National Institutes of Health. The Government has certain rights in the invention.

TECHNICAL FIELD

The present application provides radiolabeled compounds useful for imaging techniques, and more particularly to radiolabeled compounds that are useful for imaging voltage gated sodium channels and diseases related thereto. The present application further provides compounds (e.g., labeled or unlabeled compounds) useful for treating diseases associated with abnormal expression levels and/or activity of voltage gated sodium channels.

BACKGROUND

Voltage gated sodium channels (i.e., NaVs) encompass a family of nine transmembrane proteins (Nav1.1-Nav1.9) that conduct sodium currents across membranes in response to changes in membrane voltage (see e.g., Kwong & Carr, *Curr. Opin. Pharmacol.* 2015, 22:131-139). As such, they play a role in fast electrical communication by initiating and propagating action potential firing (see e.g., Bean et al, *Nat. Rev. Neurosci.* 2007, 8:451-465). While neurons of the central and peripheral nervous system contain different populations of NaVs, one isoform, NaV1.5 (and the corresponding gene, SCN5A) is found in the myocardium (see e.g., Gellens et al, *Proceedings of the National Academy of Sciences,* 1992, 89:554-558). SCN5A is the initiator of cardiac electrical signalling, and thus controls heart rate and contraction.

SUMMARY

The present application provides, inter alia, a compound of Formula I:

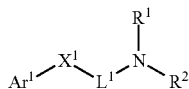

I or a pharmaceutically acceptable salt thereof, wherein:
  $X^1$ is selected from the group consisting of —O— and —NR$^N$C(O);
  $R^N$ is selected from the group consisting of H, $C_{1-6}$ alkyl, and $C_{1-6}$ haloalkyl;
  $L^1$ is a $C_{1-3}$ alkylene group;
  $Ar^1$ is selected from the group consisting of phenyl and 5-6 membered heteroaryl, wherein the phenyl and 5-6 membered heteroaryl are each optionally substituted by 1, 2, 3, 4, or 5 independently selected $R^3$ groups;
  $R^1$ is selected from the group consisting of H, $C_{1-6}$ alkyl, and $C_{1-6}$ haloalkyl;
  $R^2$ is selected from the group consisting of H, $C_{1-6}$ alkyl, $C_{1-6}$ haloalkyl, and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl; and
  each $R^3$ is independently selected from the group consisting of halo, $C_{1-6}$ alkyl, and $C_{1-6}$ haloalkyl;
  wherein the compound of Formula I comprises at least one halo or $C_{1-6}$ haloalkyl group.

In some embodiments, $X^1$ is NHC(O) or O. In some embodiments, $X^1$ is NHC(O).

In some embodiments, $L^1$ is methylene or propan-1,2-diyl. In some embodiments, $L^1$ is methylene.

In some embodiments, $R^1$ is phenyl which is optionally substituted by 1, 2, 3, 4, or 5 independently selected $R^3$ groups. In some embodiments, $R^1$ is H or $C_{1-6}$ alkyl. In some embodiments, $R^1$ is H or ethyl.

In some embodiments, $R^2$ is selected from the group consisting of $C_{1-6}$ alkyl, $C_{1-6}$ haloalkyl, and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^2$ is selected from the group consisting of $C_{1-6}$ haloalkyl and $C_{3-6}$ cycloalkyl, wherein the $C_{3-6}$ cycloalkyl group is optionally substituted by 1 or 2 substituents independently selected from the group consisting of halo and $C_{1-6}$ haloalkyl. In some embodiments, $R^2$ is $C_{1-6}$ haloalkyl. In some embodiments, $R^2$ is 2-fluoroethyl. In some embodiments, $R^2$ is H.

In some embodiments, each $R^3$ is independently selected from the group consisting of halo, $C_{1-3}$ alkyl, and $C_{1-6}$ haloalkyl. In some embodiments, each $R^3$ is independently selected from the group consisting of fluoro, $C_{1-3}$ alkyl, and $C_{1-3}$ fluoroalkyl.

In some embodiments:
  $X^1$ is NHC(O);
  $L^1$ is methylene;
  $Ar^1$ is phenyl which is optionally substituted by 1, 2, 3, 4, or 5 independently substituted $R^3$ groups;
  $R^1$ is $C_{1-6}$ alkyl;
  $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl; and
  each $R^3$ is independently selected from the group consisting of halo, $C_{1-6}$ alkyl, and $C_{1-6}$ haloalkyl.

In some embodiments:
  $X^1$ is NHC(O);
  $L^1$ is methylene;
  $Ar^1$ is phenyl which is optionally substituted by 1, 2, 3, 4, or 5 independently substituted $R^3$ groups;
  $R^1$ is $C_{1-6}$ alkyl;
  $R^2$ is selected from the group consisting of $C_{1-6}$ haloalkyl and $C_{3-6}$ cycloalkyl, wherein the $C_{3-6}$ cycloalkyl group is optionally substituted by 1 or 2 substituents independently selected from the group consisting of halo and $C_{1-6}$ haloalkyl; and each $R^3$ is independently selected from the group consisting of halo, $C_{1-6}$ alkyl, and $C_{1-6}$ haloalkyl.

In some embodiments:

$X^1$ is NHC(O);

$L^1$ is methylene;

$Ar^1$ is phenyl which is optionally substituted by 1, 2, 3, 4, or 5 independently substituted $R^3$ groups;

$R^1$ is $C_{1-6}$ alkyl;

$R^2$ is $C_{1-6}$ haloalkyl; and each $R^3$ is independently selected from the group consisting of halo, $C_{1-6}$ alkyl, and $C_{1-6}$ haloalkyl.

In some embodiments:

$X^1$ is NHC(O);

$L^1$ is methylene;

$Ar^1$ is phenyl which is optionally substituted by 1, 2, or 3 independently substituted $R^3$ groups;

$R^1$ is ethyl;

$R^2$ is $C_{1-6}$ haloalkyl; and each $R^3$ is independently selected from the group consisting of halo, $C_{1-3}$ alkyl, and $C_{1-6}$ haloalkyl.

In some embodiments:

$X^1$ is NHC(O);

$L^1$ is methylene;

$Ar^1$ is phenyl which is optionally substituted by 1, 2, or 3 independently substituted $R^3$ groups;

$R^1$ is ethyl;

$R^2$ is 2-fluoroethyl;

each $R^3$ is independently selected from the group consisting of fluoro, $C_{1-3}$ alkyl, and $C_{1-3}$ fluoroalkyl.

In some embodiments, the compound of Formula I is a compound of Formula Ia:

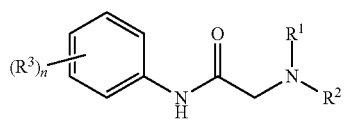

Ia or a pharmaceutically acceptable salt thereof, wherein n is an integer from 0 to 5.

In some embodiments, the compound of Formula I is a compound of Formula Ia:

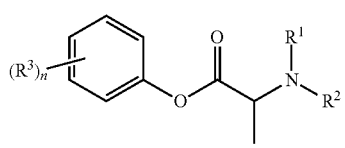

Ib or a pharmaceutically acceptable salt thereof, wherein n is an integer from 0 to 5.

In some embodiments, the compound of Formula I is a compound of Formula II:

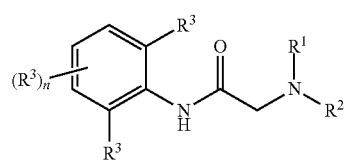

II or a pharmaceutically acceptable salt thereof, wherein n is an integer from 0 to 3.

In some embodiments, the compound of Formula I is a compound of Formula III:

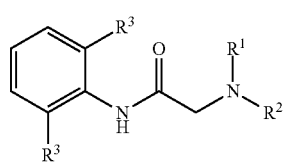

III or a pharmaceutically acceptable salt thereof.

In some embodiments, the compound of Formula I is a compound of Formula IV:

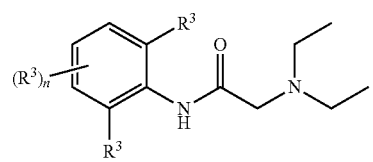

IV or a pharmaceutically acceptable salt thereof, wherein n is an integer from 0 to 3.

In some embodiments, the compound of Formula I is a compound of Formula V:

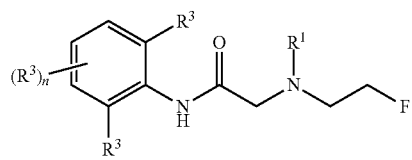

V or a pharmaceutically acceptable salt thereof, wherein n is an integer from 0 to 3.

In some embodiments, the compound of Formula I is a compound of Formula VI:

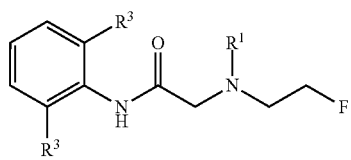

VI or a pharmaceutically acceptable salt thereof.

In some embodiments, the compound or pharmaceutically acceptable salt comprises at least one radioisotope. In some embodiments, the compound or pharmaceutically acceptable salt comprises at least one radioisotope selected from the group consisting of $^{11}$C, $^{13}$N, and $^{18}$F. In some embodiments, the compound or pharmaceutically acceptable salt comprises at least one $^{18}$F radioisotope In some embodiments, the compound of Formula I is a compound of Formula VII:

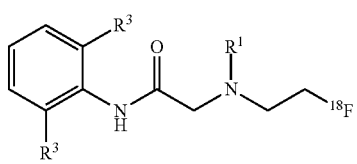

or a pharmaceutically acceptable salt thereof.

In some embodiments, the compound of Formula I is selected from the group consisting of:

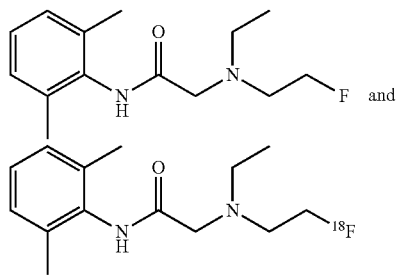

or a pharmaceutically acceptable salt thereof.

In some embodiments, the compound of Formula I is:

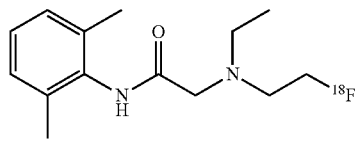 [SMILES: CCN(CC[18F])CC(=O)Nc1c(C)cccc1C]

or a pharmaceutically acceptable salt thereof.

The present application further provides a pharmaceutical composition comprising a compound provided herein, or a pharmaceutically acceptable salt thereof, and at least one pharmaceutically acceptable carrier.

The present application further provides a method of blocking one or more isoforms of voltage gated sodium channels in a cell sample or tissue sample, comprising contacting the cell sample or tissue sample with a compound provided herein, or a pharmaceutically acceptable salt thereof.

The present application further provides a method of blocking one or more isoforms of voltage gated sodium channels in a subject, comprising administering to the subject a compound provided herein, or a pharmaceutically acceptable salt thereof.

In some embodiments, the method comprises blocking sodium channel Nav1.5.

The present application further provides a method of imaging one or more voltage gated sodium channel isoforms in a cell sample or tissue sample, comprising:

i) contacting the cell sample or tissue sample with a radiolabeled compound provided herein, or a pharmaceutically acceptable salt thereof; and
ii) imaging the cell sample or tissue sample with an imaging technique.

The present application further provides a method of imaging one or more voltage gated sodium channel isoforms in a subject, comprising:

i) administering to the subject a radiolabeled compound provided herein, or a pharmaceutically acceptable salt thereof, and
ii) imaging the subject with an imaging technique.

In some embodiments, the method comprises imaging sodium channel Nav1.5.

The present application further provides a method of imaging the heart in a subject, comprising:

i) administering to the subject a radiolabeled compound provided herein, or a pharmaceutically acceptable salt thereof, and
ii) imaging the subject with an imaging technique.

The present application further provides a method of imaging the spinal cord in a subject, comprising:

i) administering to the subject a radiolabeled compound provided herein, or a pharmaceutically acceptable salt thereof, and
ii) imaging the subject with an imaging technique.

The present application further provides a method of imaging a tumor in a subject, comprising:

i) administering to the subject a radiolabeled compound provided herein, or a pharmaceutically acceptable salt thereof, and
ii) imaging the subject with an imaging technique.

The present application further provides a method of monitoring treatment of a disease associated with abnormal expression levels of one or more voltage gated sodium channel isoforms in a subject, comprising:

i) imaging the subject with an imaging technique;
ii) administering to the subject a therapeutically effective amount of a compound provided herein, or a pharmaceutically acceptable salt thereof;
iii) imaging the subject with an imaging technique; and
iv) comparing the image of step i) and the image of step iii).

The present application further provides a method of monitoring treatment of a disease associated with abnormal activity of one or more voltage gated sodium channel isoforms in a subject, comprising:

i) imaging the subject with an imaging technique;
ii) administering to the subject a therapeutically effective amount of a compound provided herein, or a pharmaceutically acceptable salt thereof;
iii) imaging the subject with an imaging technique; and
iv) comparing the image of step i) and the image of step iii).

The present application further provides a method of imaging a disease associated with abnormal expression levels of one or more voltage gated sodium channel isoforms, the method comprising:

i) administering to the subject a radiolabeled compound provided herein, or a pharmaceutically acceptable salt thereof, and
ii) imaging the subject with an imaging technique.

In some embodiments, the imaging technique is selected from the group consisting of single-photon emission computed tomography, positron emission tomography imaging, computed tomography, positron emission tomography with computed tomography imaging, positron emission tomography with magnetic resonance imaging. In some embodiments, the imaging technique is positron emission tomography imaging.

In some embodiments, the disease is associated with abnormal expression levels of voltage gated sodium channel Nav1.5. In some embodiments, the disease is associated with low expression levels of voltage gated sodium channel Nav1.5 in the subject compared to the expression levels of sodium channel Nav1.5 in a control subject. In some embodiments, the disease is associated with abnormal activity of voltage gated sodium channel Nav1.5 in the subject compared to the activity of sodium channel Nav1.5 in a control subject.

In some embodiments, the disease is selected from the group consisting of cardiovascular disease, neurological disease, and cancer. In some embodiments, the cardiovascular disease comprises cardiac arrhythmia. In some embodiments, the cardiovascular disease is selected from the group consisting of cardiomyopathy, ventricular fibrillation, tachycardia, myocardial infarction, long QT syndrome, Brugada syndrome, progressive cardiac conduction disease, sick sinus syndrome, atrial fibrillation, hypertension, myocarditis, and heart failure.

In some embodiments, the neurological disease is selected from the group consisting of multiple sclerosis, amyotrophic lateral sclerosis, neuropathic pain, diabetic pain, cancer pain, trigeminal neuralgia.

In some embodiments, the cancer is selected from the group consisting of breast cancer, prostate cancer, and small cell lung cancer, and non-small cell lung cancer.

The present application further provides a process of preparing a compound of Formula VIII:

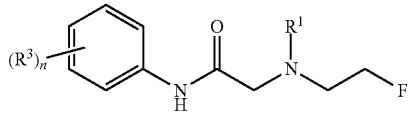

VIII or a salt thereof, comprising reacting a compound of Formula Ic:

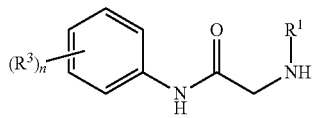

Ic with a compound of Formula IX:

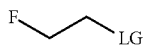

IX in the presence of a base, wherein:
  LG is a leaving group;
  $R^1$ is selected from the group consisting of H, $C_{1-6}$ alkyl, and $C_{1-6}$ haloalkyl;
  each $R^3$ is independently selected from the group consisting of halo, $C_{1-6}$ alkyl, and $C_{1-6}$ haloalkyl; and
  n is an integer from 0 to 5.

In some embodiments, the base is a carbonate base. In some embodiments, the base is potassium carbonate.

In some embodiments, the reacting is performed at a temperature of about 50° C. to about 150° C.

In some embodiments, about 1 to about 1.5 equivalents of the compound of Formula IX is used based on 1 equivalent of the compound of Formula Ic.

The present application further provides a process of preparing a compound of Formula X:

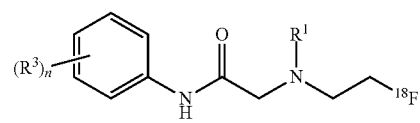

X or a salt thereof, comprising reacting a compound of Formula Ic:

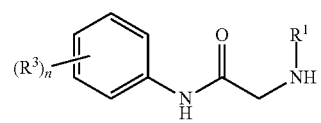

Ic with a compound of Formula IXa:

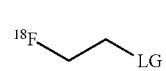

IXa wherein:
  LG is a leaving group;
  $R^1$ is selected from the group consisting of H, $C_{1-6}$ alkyl, and $C_{1-6}$ haloalkyl;
  each $R^3$ is independently selected from the group consisting of halo, $C_{1-6}$ alkyl, and $C_{1-6}$ haloalkyl; and
  n is an integer from 0 to 5.

In some embodiments, the reacting is performed at a temperature of about 50° C. to about 150° C.

In some embodiments, LG is a leaving group selected from the group consisting of tosylate and mesylate. In some embodiments, LG is a tosylate group.

In some embodiments, the reacting is performed in a solvent. In some embodiments, the solvent is a polar aprotic solvent or a polar protic solvent. In some embodiments, the solvent is selected from the group consisting of dimethylformamide and acetonitrile.

The present application further provides a process of preparing a compound of the following formula:

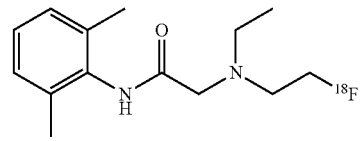 [SMILES: CCN(CC[18F])CC(=O)Nc1c(C)cccc1C]

or a salt thereof, comprising reacting N-(2,6-dimethylphenyl)-2-(ethylamino)acetamide with 2-(fluoro-$^{18}$F)ethyl 4-methylbenzenesulfonate, wherein the reacting is performed in a polar aprotic solvent.

In some embodiments, the reacting is performed as a one-pot synthesis.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1A:
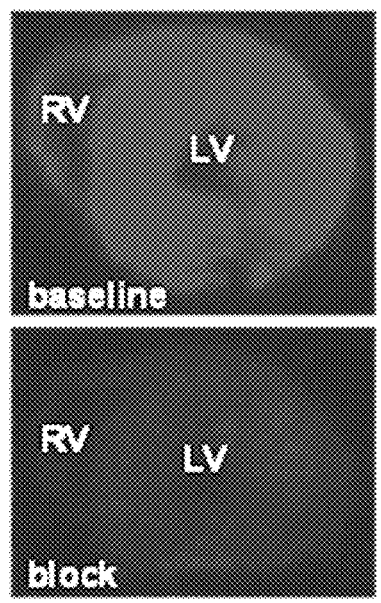
FIG. 1A shows images of rat myocardial tissue slices (20 μm) incubated with N-(2,6-dimethylphenyl)-2-(ethyl(2-(fluoro-$^{18}$F)ethyl)amino)acetamide (top) or N-(2,6-dimethylphenyl)-2-(ethyl(2-(fluoro-$^{18}$F)ethyl)amino)acetamide and 500 μM N-(2,6-dimethylphenyl)-2-(ethyl(2-fluoroethyl)amino)acetamide (bottom). Both the left and right ventricle (LV & RV) are visible and surrounded by the myocardium, which displayed a strong radioactive signal. Suppression of this signal by coincubation with N-(2,6-dimethylphenyl)-2-(ethyl(2-fluoroethyl)amino)acetamide demonstrated displaceable binding.

Although SCN5A, and the corresponding sodium voltage-gated channel alpha subunit 5 (NaV1.5), is thought to be a potentially important component in cardiac function, there is a lack of knowledge about its expression density in healthy individuals and as a function of disease. For example, current methods are unable to measure SCN5A density in patients to gauge response to therapies such as antiarrythmic agents or cardiac pacemakers/defibrillators, and it has not been possible to quantify drug occupancy levels at NaV1.5 that are efficacious. The compounds and radiolabeled compounds provided herein engage SCN5A in the myocardium and addresses the need for agents which are useful for monitoring levels of SCN5A and NaV1.5.

Compounds

The present application provides a compound of Formula I:

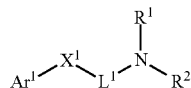
I or a pharmaceutically acceptable salt thereof, wherein:
$X^1$ is selected from the group consisting of —O— and —NR$^N$C(O)—;
$R^N$ is selected from the group consisting of H, $C_{1-6}$ alkyl, and $C_{1-6}$ haloalkyl;
$L^1$ is a $C_{1-3}$ alkylene group;
$Ar^1$ is selected from the group consisting of phenyl and 5-6 membered heteroaryl, wherein the phenyl and 5-6 membered heteroaryl are each optionally substituted by 1, 2, 3, 4, or 5 independently selected $R^3$ groups;
$R^1$ is selected from the group consisting of H, $C_{1-6}$ alkyl, and $C_{1-6}$ haloalkyl;
$R^2$ is selected from the group consisting of H, $C_{1-6}$ alkyl, $C_{1-6}$ haloalkyl, and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl; and
each $R^3$ is independently selected from the group consisting of halo, $C_{1-6}$ alkyl, and $C_{1-6}$ haloalkyl.

In some embodiments, the compound provided herein is not a compound selected from the group consisting of:

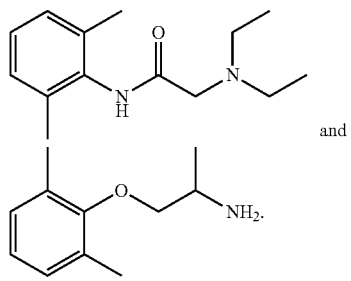

and

In some embodiments, $X^1$ is O. In some embodiments, $X^1$ is —NR$^N$C(O)—. In some embodiments, $X^1$ is —NHC(O)—.

In some embodiments, $L^1$ is methylene. In some embodiments, $L^1$ is propan-1,2-diyl.

In some embodiments, $Ar^1$ is phenyl which is optionally substituted by 1, 2, 3, 4, or 5 independently selected $R^3$ groups. In some embodiments, $Ar^1$ is phenyl which is optionally substituted by 1, 2 or 3 independently selected $R^3$ groups. In some embodiments, $Ar^1$ is phenyl which is optionally substituted by 1 or 2 independently selected $R^3$ groups. In some embodiments, $Ar^1$ is:

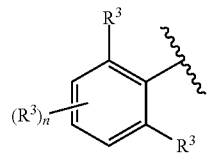

wherein ⁓ indicates the bond between $Ar^1$ and $X^1$ and n is an integer from 0 to 3. In some embodiments, $Ar^1$ is:

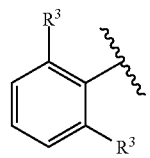

wherein ⁓ indicates the bond between $Ar^1$ and $X^1$.

In some embodiments, $Ar^1$ is a 5-6 membered heteroaryl group which is optionally substituted by 1, 2, 3, 4, or 5 independently selected $R^3$ groups. In some embodiments, $Ar^1$ is a 5-6 membered heteroaryl group which is optionally substituted by 1, 2, or 3 independently selected $R^3$ groups. In some embodiments, $Ar^1$ is a 5-6 membered heteroaryl group which is optionally substituted by 1 or 2 independently selected $R^3$ groups. In some embodiments, the 5-6 membered heteroaryl group of $Ar^1$ comprises 1, 2, or 3 heteroatom ring members independently selected from N and S.

In some embodiments, $R^1$ is $C_{1-6}$ alkyl. In some embodiments, $R^1$ is $C_{1-3}$ alkyl. In some embodiments, $R^1$ is ethyl. In some embodiments, $R^1$ is H.

In some embodiments, $R^2$ is selected from the group consisting of $C_{1-6}$ alkyl, $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of fluoro and $C_{1-6}$ fluoroalkyl. In some embodiments, $R^2$ is selected from the group consisting of $C_{1-6}$ haloalkyl and $C_{3-6}$ cycloalkyl, wherein the $C_{3-6}$ cycloalkyl group is optionally substituted by 1 or 2 substituents independently selected from the group consisting of halo and $C_{1-6}$ haloalkyl. In some embodiments, $R^2$ is selected from the group consisting of $C_{1-6}$ haloalkyl and $C_{3-6}$ cycloalkyl, wherein the $C_{3-6}$ cycloalkyl group is optionally substituted by 1 or 2 substituents independently selected from the group consisting of fluoro and $C_{1-6}$ fluoroalkyl. In some embodiments, $R^2$ is $C_{1-6}$ haloalkyl. In some embodiments, $R^2$ is $C_{1-6}$ fluoroalkyl. In some embodiments, $R^2$ is 2-fluoroethyl. In some embodiments, $R^2$ is H.

In some embodiments, $R^1$ and $R^2$ are each H. In some embodiments, $R^1$ is H and $R^2$ is selected from the group consisting of $C_{1-6}$ alkyl, $C_{1-6}$ haloalkyl, and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^1$ is H and $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^1$ is H and $R^2$ is $C_{1-6}$ haloalkyl. In some embodiments, $R^1$ is H and $R^2$ is $C_{1-6}$ fluoroalkyl. In some embodiments, $R^1$ is $C_{1-6}$ alkyl and $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^1$ is $C_{1-3}$ alkyl and $R^2$ is $C_{1-6}$ haloalkyl. In some embodiments, $R^1$ is $C_{1-3}$ alkyl and $R^2$ is $C_{1-6}$ fluoroalkyl.

In some embodiments, each $R^3$ is independently selected from the group consisting of halo, $C_{1-3}$ alkyl, and $C_{1-6}$ haloalkyl. In some embodiments, each $R^3$ is independently selected from the group consisting of halo, $C_{1-6}$ alkyl, and $C_{1-3}$ haloalkyl. In some embodiments, each $R^3$ is independently selected from the group consisting of halo, $C_{1-3}$ alkyl, and $C_{1-3}$ haloalkyl. In some embodiments, each $R^3$ is independently selected from the group consisting of halo, $C_{1-6}$ alkyl, and $C_{1-6}$ fluoroalkyl. In some embodiments, each $R^3$ is independently selected from the group consisting of halo, $C_{1-3}$ alkyl, and $C_{1-6}$ fluoroalkyl. In some embodiments, each $R^3$ is independently selected from the group consisting of halo, $C_{1-6}$ alkyl, and $C_{1-3}$ fluoroalkyl. In some embodiments, each $R^3$ is independently selected from the group consisting of halo, $C_{1-3}$ alkyl, and $C_{1-3}$ fluoroalkyl. In some embodiments, each $R^3$ is independently selected from the group consisting of fluoro, $C_{1-6}$ alkyl, and $C_{1-6}$ haloalkyl. In some embodiments, each $R^3$ is independently selected from the group consisting of fluoro, $C_{1-3}$ alkyl, and $C_{1-6}$ fluoroalkyl. In some embodiments, each $R^3$ is independently selected from the group consisting of fluoro, $C_{1-6}$ alkyl, and $C_{1-3}$ fluoroalkyl. In some embodiments, each $R^3$ is independently selected from the group consisting of fluoro, $C_{1-3}$ alkyl, and $C_{1-3}$ fluoroalkyl.

In some embodiments:
- $X^1$ is O or NHC(O);
- $L^1$ is $C_{1-3}$ alkylene;
- $Ar^1$ is phenyl which is optionally substituted by 1, 2, 3, 4, or 5 independently substituted $R^3$ groups;
- $R^1$ is selected from the group consisting of H, $C_{1-6}$ alkyl, and $C_{1-6}$ haloalkyl;
- $R^2$ is selected from the group consisting of $C_{1-6}$ alkyl, $C_{1-6}$ haloalkyl, and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl; and
- each $R^3$ is independently selected from the group consisting of halo, $C_{1-6}$ alkyl, and $C_{1-6}$ haloalkyl.

In some embodiments:
- $X^1$ is NHC(O);
- $L^1$ is $C_{1-3}$ alkylene;
- $Ar^1$ is phenyl which is optionally substituted by 1, 2, 3, 4, or 5 independently substituted $R^3$ groups;
- $R^1$ is selected from the group consisting of H, $C_{1-6}$ alkyl, and $C_{1-6}$ haloalkyl;
- $R^2$ is selected from the group consisting of $C_{1-6}$ alkyl, $C_{1-6}$ haloalkyl, and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl; and
- each $R^3$ is independently selected from the group consisting of halo, $C_{1-6}$ alkyl, and $C_{1-6}$ haloalkyl.

In some embodiments:
- $X^1$ is NHC(O);
- $L^1$ is methylene;
- $Ar^1$ is phenyl which is optionally substituted by 1, 2, 3, 4, or 5 independently substituted $R^3$ groups;
- $R^1$ is selected from the group consisting of H, $C_{1-6}$ alkyl, and $C_{1-6}$ haloalkyl;
- $R^2$ is selected from the group consisting of $C_{1-6}$ alkyl, $C_{1-6}$ haloalkyl, and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl; and
- each $R^3$ is independently selected from the group consisting of halo, $C_{1-6}$ alkyl, and $C_{1-6}$ haloalkyl.

In some embodiments:
- $X^1$ is NHC(O);
- $L^1$ is methylene;
- $Ar^1$ is phenyl which is optionally substituted by 1, 2, 3, 4, or 5 independently substituted $R^3$ groups;
- $R^1$ is $C_{1-6}$ alkyl;
- $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl; and
- each $R^3$ is independently selected from the group consisting of halo, $C_{1-6}$ alkyl, and $C_{1-6}$ haloalkyl.

In some embodiments:
- $X^1$ is NHC(O);
- $L^1$ is methylene;
- $Ar^1$ is phenyl which is optionally substituted by 1, 2, 3, 4, or 5 independently substituted $R^3$ groups;
- $R^1$ is $C_{1-6}$ alkyl;
- $R^2$ is selected from the group consisting of $C_{1-6}$ haloalkyl and $C_{3-6}$ cycloalkyl, wherein the $C_{3-6}$ cycloalkyl group is optionally substituted by 1 or 2 substituents independently selected from the group consisting of halo and $C_{1-6}$ haloalkyl; and
- each $R^3$ is independently selected from the group consisting of halo, $C_{1-6}$ alkyl, and $C_{1-6}$ haloalkyl.

In some embodiments:
- $X^1$ is NHC(O);
- $L^1$ is methylene;
- $Ar^1$ is phenyl which is optionally substituted by 1, 2, 3, 4, or 5 independently substituted $R^3$ groups;
- $R^1$ is $C_{1-6}$ alkyl;
- $R^2$ is selected from the group consisting of $C_{1-6}$ fluoroalkyl and $C_{3-6}$ cycloalkyl, wherein the $C_{3-6}$ cycloalkyl group is optionally substituted by 1 or 2 substituents independently selected from the group consisting of halo and $C_{1-6}$ haloalkyl; and
- each $R^3$ is independently selected from the group consisting of halo, $C_{1-3}$ alkyl, and $C_{1-3}$ haloalkyl.

In some embodiments:
- $X^1$ is NHC(O);
- $L^1$ is methylene;
- $Ar^1$ is phenyl which is optionally substituted by 1, 2, 3, 4, or 5 independently substituted $R^3$ groups;
- $R^1$ is $C_{1-6}$ alkyl;
- $R^2$ is selected from the group consisting of $C_{1-3}$ fluoroalkyl and $C_{3-6}$ cycloalkyl, wherein the $C_{3-6}$ cycloalkyl group is optionally substituted by 1 or 2 substituents independently selected from the group consisting of fluoro and $C_{1-3}$ fluoroalkyl; and
- each $R^3$ is independently selected from the group consisting of fluoro, $C_{1-3}$ alkyl, and $C_{1-3}$ fluoroalkyl.

In some embodiments:
X¹ is NHC(O);
L¹ is methylene;
Ar¹ is phenyl which is optionally substituted by 1, 2, 3, 4, or 5 independently substituted R³ groups;
R¹ is $C_{1-6}$ alkyl;
R² is $C_{1-6}$ haloalkyl; and
each R³ is independently selected from the group consisting of halo, $C_{1-6}$ alkyl, and $C_{1-6}$ haloalkyl.

In some embodiments:
X¹ is NHC(O);
L¹ is methylene;
Ar¹ is phenyl which is optionally substituted by 1, 2, 3, 4, or 5 independently substituted R³ groups;
R¹ is $C_{1-3}$ alkyl;
R² is $C_{1-3}$ fluoroalkyl; and
each R³ is independently selected from the group consisting of fluoro, $C_{1-3}$ alkyl, and $C_{1-6}$ fluoroalkyl.

In some embodiments:
X¹ is NHC(O);
L¹ is methylene;
Ar¹ is phenyl which is optionally substituted by 1, 2, 3, 4, or 5 independently substituted R³ groups;
R¹ is ethyl;
R² is $C_{1-6}$ haloalkyl; and
each R³ is independently selected from the group consisting of halo, $C_{1-3}$ alkyl, and $C_{1-6}$ haloalkyl.

In some embodiments:
X¹ is NHC(O);
L¹ is methylene;
Ar¹ is phenyl which is optionally substituted by 1, 2, or 3 independently substituted R³ groups;
R¹ is ethyl;
R² is $C_{1-3}$ haloalkyl; and
each R³ is independently selected from the group consisting of halo, $C_{1-3}$ alkyl, and $C_{1-3}$ haloalkyl.

In some embodiments:
X¹ is NHC(O);
L¹ is methylene;
Ar¹ is phenyl which is optionally substituted by 1, 2, or 3 independently substituted R³ groups;
R¹ is ethyl;
R² is 2-fluoroethyl;
each R³ is independently selected from the group consisting of fluoro, $C_{1-3}$ alkyl, and $C_{1-3}$ fluoroalkyl.

In some embodiments:
X¹ is O;
L¹ is $C_{1-3}$ alkylene;
Ar¹ is phenyl which is optionally substituted by 1, 2, 3, 4, or 5 independently substituted R³ groups;
R¹ and R² are each H; and
each R³ is independently selected from the group consisting of halo, $C_{1-6}$ alkyl, and $C_{1-6}$ haloalkyl.

In some embodiments:
X¹ is O;
L¹ is propan-1,2-diyl;
Ar¹ is phenyl which is optionally substituted by 1, 2, or 3 independently substituted R³ groups;
R¹ and R² are each H; and
each R³ is independently selected from the group consisting of halo, $C_{1-3}$ alkyl, and $C_{1-3}$ haloalkyl.

In some embodiments:
X¹ is O;
L¹ is propan-1,2-diyl;
Ar¹ is phenyl which is optionally substituted by 1, 2, or 3 independently substituted R³ groups;
R¹ and R² are each H; and
each R³ is independently selected from the group consisting of fluoro, $C_{1-3}$ alkyl, and $C_{1-3}$ fluoroalkyl.

In some embodiments, the compound of Formula I is a compound of Formula Ia:

or a pharmaceutically acceptable salt thereof, wherein n is an integer from 0 to 5 and variables R¹, R² and R³ are defined according to the definitions provided herein for compounds of Formula I.

In some embodiments, R¹ is $C_{1-6}$ alkyl. In some embodiments, R¹ is $C_{1-3}$ alkyl. In some embodiments, R¹ is ethyl.

In some embodiments, R² is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, R² is selected from the group consisting of $C_{1-6}$ haloalkyl and $C_{3-6}$ cycloalkyl, wherein the $C_{3-6}$ cycloalkyl group is optionally substituted by 1 or 2 substituents independently selected from the group consisting of halo and $C_{1-6}$ haloalkyl. In some embodiments, R² is $C_{1-6}$ haloalkyl. In some embodiments, R² is $C_{1-6}$ fluoroalkyl. In some embodiments, R² is 2-fluoroethyl.

In some embodiments, R¹ is $C_{1-6}$ alkyl and R² is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, R¹ is $C_{1-3}$ alkyl and R² is $C_{1-6}$ haloalkyl. In some embodiments, R¹ is $C_{1-3}$ alkyl and R² is $C_{1-6}$ fluoroalkyl.

In some embodiments, each R³ is independently selected from the group consisting of halo, $C_{1-3}$ alkyl, and $C_{1-6}$ haloalkyl. In some embodiments, each R³ is independently selected from the group consisting of halo, $C_{1-6}$ alkyl, and $C_{1-3}$ haloalkyl. In some embodiments, each R³ is independently selected from the group consisting of halo, $C_{1-3}$ alkyl, and $C_{1-3}$ haloalkyl. In some embodiments, each R³ is independently selected from the group consisting of halo, $C_{1-6}$ alkyl, and $C_{1-6}$ fluoroalkyl. In some embodiments, each R³ is independently selected from the group consisting of halo, $C_{1-3}$ alkyl, and $C_{1-6}$ fluoroalkyl. In some embodiments, each R³ is independently selected from the group consisting of halo, $C_{1-6}$ alkyl, and $C_{1-3}$ fluoroalkyl. In some embodiments, each R³ is independently selected from the group consisting of halo, $C_{1-3}$ alkyl, and $C_{1-3}$ fluoroalkyl. In some embodiments, each R³ is independently selected from the group consisting of fluoro, $C_{1-6}$ alkyl, and $C_{1-6}$ haloalkyl. In some embodiments, each R³ is independently selected from the group consisting of fluoro, $C_{1-3}$ alkyl, and $C_{1-6}$ fluoroalkyl. In some embodiments, each R³ is independently selected from the group consisting of fluoro, $C_{1-6}$ alkyl, and $C_{1-3}$ fluoroalkyl. In some embodiments, each R³ is independently selected from the group consisting of fluoro, $C_{1-3}$ alkyl, and $C_{1-3}$ fluoroalkyl. In some embodiments, each R³ is an independently selected $C_{1-3}$ alkyl group. In some embodiments, each R³ is methyl.

In some embodiments, n is an integer from 0 to 3. In some embodiments, n is 0. In some embodiments, n is 1. In some embodiments, n is 2. In some embodiments, n is 3.

In some embodiments, the compound of Formula I is a compound of Formula Ib:

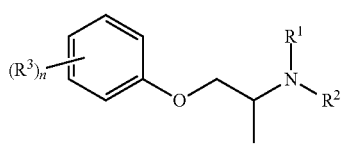

Ib or a pharmaceutically acceptable salt thereof, wherein n is an integer from 0 to 5 and variables $R^1$, $R^2$ and $R^3$ are defined according to the definitions provided herein for compounds of Formula I.

In some embodiments, the compound of Formula I, or a pharmaceutically acceptable salt thereof, is a compound of Formula II:

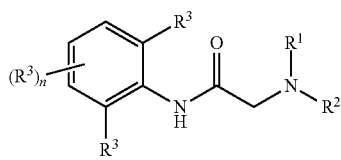

II or a pharmaceutically acceptable salt thereof, wherein n is an integer from 0 to 3 and variables $R^1$, $R^2$, and $R^3$ are defined according to the definitions provided herein for compounds of Formula I.

In some embodiments, $R^1$ is $C_{1-6}$ alkyl. In some embodiments, $R^1$ is $C_{1-3}$ alkyl. In some embodiments, $R^1$ is ethyl.

In some embodiments, $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^2$ is selected from the group consisting of $C_{1-6}$ haloalkyl and $C_{3-6}$ cycloalkyl, wherein the $C_{3-6}$ cycloalkyl group is optionally substituted by 1 or 2 substituents independently selected from the group consisting of halo and $C_{1-6}$ haloalkyl. In some embodiments, $R^2$ is $C_{1-6}$ haloalkyl. In some embodiments, $R^2$ is $C_{1-6}$ fluoroalkyl. In some embodiments, $R^2$ is 2-fluoroethyl.

In some embodiments, $R^1$ is $C_{1-6}$ alkyl and $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^1$ is $C_{1-3}$ alkyl and $R^2$ is $C_{1-6}$ haloalkyl. In some embodiments, $R^1$ is $C_{1-3}$ alkyl and $R^2$ is $C_{1-6}$ fluoroalkyl.

In some embodiments, each $R^3$ is independently selected from the group consisting of halo, $C_{1-3}$ alkyl, and $C_{1-6}$ haloalkyl. In some embodiments, each $R^3$ is independently selected from the group consisting of halo, $C_{1-6}$ alkyl, and $C_{1-3}$ haloalkyl.

In some embodiments, each $R^3$ is independently selected from the group consisting of halo, $C_{1-3}$ alkyl, and $C_{1-3}$ haloalkyl. In some embodiments, each $R^3$ is independently selected from the group consisting of halo, $C_{1-6}$ alkyl, and $C_{1-6}$ fluoroalkyl. In some embodiments, each $R^3$ is independently selected from the group consisting of halo, $C_{1-3}$ alkyl, and $C_{1-6}$ fluoroalkyl. In some embodiments, each $R^3$ is independently selected from the group consisting of halo, $C_{1-6}$ alkyl, and $C_{1-3}$ fluoroalkyl. In some embodiments, each $R^3$ is independently selected from the group consisting of fluoro, $C_{1-6}$ alkyl, and $C_{1-6}$ haloalkyl. In some embodiments, each $R^3$ is independently selected from the group consisting of fluoro, $C_{1-3}$ alkyl, and $C_{1-6}$ fluoroalkyl. In some embodiments, each $R^3$ is independently selected from the group consisting of fluoro, $C_{1-6}$ alkyl, and $C_{1-3}$ fluoroalkyl. In some embodiments, each $R^3$ is independently selected from the group consisting of fluoro, $C_{1-3}$ alkyl, and $C_{1-3}$ fluoroalkyl. In some embodiments, each $R^3$ is an independently selected $C_{1-3}$ alkyl group. In some embodiments, each $R^3$ is methyl.

In some embodiments, n is 0 or 1. In some embodiments, n is 0.

In some embodiments, the compound of Formula I, or a pharmaceutically acceptable salt thereof, is a compound of Formula III:

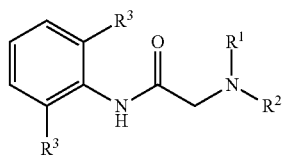

III or a pharmaceutically acceptable salt thereof, wherein variables $R^1$, $R^2$, and $R^3$ are defined according to the definitions provided herein for compounds of Formula I.

In some embodiments, $R^1$ is $C_{1-6}$ alkyl. In some embodiments, $R^1$ is $C_{1-3}$ alkyl. In some embodiments, $R^1$ is ethyl.

In some embodiments, $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^2$ is selected from the group consisting of $C_{1-6}$ haloalkyl and $C_{3-6}$ cycloalkyl, wherein the $C_{3-6}$ cycloalkyl group is optionally substituted by 1 or 2 substituents independently selected from the group consisting of halo and $C_{1-6}$ haloalkyl. In some embodiments, $R^2$ is $C_{1-6}$ haloalkyl. In some embodiments, $R^2$ is $C_{1-6}$ fluoroalkyl. In some embodiments, $R^2$ is 2-fluoroethyl.

In some embodiments, $R^1$ is $C_{1-6}$ alkyl and $R^2$ is selected from the group consisting of $C_{1-6}$ haloalkyl and $C_{3-10}$ cycloalkyl, wherein the $C_{3-10}$ cycloalkyl group is optionally substituted by 1, 2, 3, or 4 substituents independently selected from the group consisting of halo and $C_{1-6}$ haloalkyl. In some embodiments, $R^1$ is $C_{1-3}$ alkyl and $R^2$ is $C_{1-6}$ haloalkyl. In some embodiments, $R^1$ is $C_{1-3}$ alkyl and $R^2$ is $C_{1-6}$ fluoroalkyl.

In some embodiments, each $R^3$ is independently selected from the group consisting of halo, $C_{1-3}$ alkyl, and $C_{1-6}$ haloalkyl. In some embodiments, each $R^3$ is independently selected from the group consisting of halo, $C_{1-6}$ alkyl, and $C_{1-3}$ haloalkyl. In some embodiments, each $R^3$ is independently selected from the group consisting of halo, $C_{1-3}$ alkyl, and $C_{1-3}$ haloalkyl. In some embodiments, each $R^3$ is independently selected from the group consisting of halo, $C_{1-6}$ alkyl, and $C_{1-6}$ fluoroalkyl. In some embodiments, each $R^3$ is independently selected from the group consisting of halo, $C_{1-3}$ alkyl, and $C_{1-6}$ fluoroalkyl. In some embodiments, each $R^3$ is independently selected from the group consisting of halo, $C_{1-6}$ alkyl, and $C_{1-3}$ fluoroalkyl. In some embodiments, each $R^3$ is independently selected from the group consisting of halo, $C_{1-3}$ alkyl, and $C_{1-3}$ fluoroalkyl. In some embodiments, each $R^3$ is independently selected from the group consisting of fluoro, $C_{1-6}$ alkyl, and $C_{1-6}$ haloalkyl. In some embodiments, each $R^3$ is independently selected from the group consisting of fluoro, $C_{1-3}$ alkyl, and $C_{1-6}$ fluoroalkyl. In some embodiments, each $R^3$ is independently selected from the group consisting of fluoro, $C_{1-6}$ alkyl, and $C_{1-3}$ fluoroalkyl. In some embodiments, each $R^3$ is independently selected from the group consisting of fluoro, $C_{1-3}$ alkyl, and $C_{1-3}$ fluoroalkyl. In some embodiments, each $R^3$ is an independently selected $C_{1-3}$ alkyl group. In some embodiments, each $R^3$ is methyl.

In some embodiments, the compound of Formula I, or a pharmaceutically acceptable salt thereof, is a compound of Formula IV:

or a pharmaceutically acceptable salt thereof, wherein n is an integer from 0 to 3, and variable $R^3$ is defined according to the definitions provided herein for compounds of Formula I.

In some embodiments, each $R^3$ is independently selected from the group consisting of halo, $C_{1-3}$ alkyl, and $C_{1-6}$ haloalkyl. In some embodiments, each $R^3$ is independently selected from the group consisting of halo, $C_{1-6}$ alkyl, and $C_{1-3}$ haloalkyl. In some embodiments, each $R^3$ is independently selected from the group consisting of halo, $C_{1-3}$ alkyl, and $C_{1-3}$ haloalkyl. In some embodiments, each $R^3$ is independently selected from the group consisting of halo, $C_{1-6}$ alkyl, and $C_{1-6}$ fluoroalkyl. In some embodiments, each $R^3$ is independently selected from the group consisting of halo, $C_{1-3}$ alkyl, and $C_{1-6}$ fluoroalkyl. In some embodiments, each $R^3$ is independently selected from the group consisting of halo, $C_{1-6}$ alkyl, and $C_{1-3}$ fluoroalkyl. In some embodiments, each $R^3$ is independently selected from the group consisting of halo, $C_{1-3}$ alkyl, and $C_{1-3}$ fluoroalkyl. In some embodiments, each $R^3$ is independently selected from the group consisting of fluoro, $C_{1-6}$ alkyl, and $C_{1-6}$ haloalkyl. In some embodiments, each $R^3$ is independently selected from the group consisting of fluoro, $C_{1-3}$ alkyl, and $C_{1-6}$ fluoroalkyl. In some embodiments, each $R^3$ is independently selected from the group consisting of fluoro, $C_{1-6}$ alkyl, and $C_{1-3}$ fluoroalkyl. In some embodiments, each $R^3$ is independently selected from the group consisting of fluoro, $C_{1-3}$ alkyl, and $C_{1-3}$ fluoroalkyl. In some embodiments, each $R^3$ is an independently selected $C_{1-3}$ alkyl group. In some embodiments, each $R^3$ is methyl.

In some embodiments, n is 0 or 1. In some embodiments, n is 0.

In some embodiments, the compound of Formula I, or a pharmaceutically acceptable salt thereof, is a compound of Formula V:

or a pharmaceutically acceptable salt thereof, wherein n is an integer from 0 to 3, and variables $R^1$ and $R^3$ are defined according to the definitions provided herein for compounds of Formula I.

In some embodiments, $R^1$ is $C_{1-6}$ alkyl. In some embodiments, $R^1$ is $C_{1-3}$ alkyl. In some embodiments, $R^1$ is ethyl.

In some embodiments, each $R^3$ is independently selected from the group consisting of halo, $C_{1-3}$ alkyl, and $C_{1-6}$ haloalkyl. In some embodiments, each $R^3$ is independently selected from the group consisting of halo, $C_{1-6}$ alkyl, and $C_{1-3}$ haloalkyl. In some embodiments, each $R^3$ is independently selected from the group consisting of halo, $C_{1-3}$ alkyl, and $C_{1-3}$ haloalkyl. In some embodiments, each $R^3$ is independently selected from the group consisting of halo, $C_{1-6}$ alkyl, and $C_{1-6}$ fluoroalkyl. In some embodiments, each $R^3$ is independently selected from the group consisting of halo, $C_{1-3}$ alkyl, and $C_{1-6}$ fluoroalkyl. In some embodiments, each $R^3$ is independently selected from the group consisting of halo, $C_{1-6}$ alkyl, and $C_{1-3}$ fluoroalkyl. In some embodiments, each $R^3$ is independently selected from the group consisting of halo, $C_{1-3}$ alkyl, and $C_{1-3}$ fluoroalkyl. In some embodiments, each $R^3$ is independently selected from the group consisting of fluoro, $C_{1-6}$ alkyl, and $C_{1-6}$ haloalkyl. In some embodiments, each $R^3$ is independently selected from the group consisting of fluoro, $C_{1-3}$ alkyl, and $C_{1-6}$ fluoroalkyl. In some embodiments, each $R^3$ is independently selected from the group consisting of fluoro, $C_{1-6}$ alkyl, and $C_{1-3}$ fluoroalkyl. In some embodiments, each $R^3$ is independently selected from the group consisting of fluoro, $C_{1-3}$ alkyl, and $C_{1-3}$ fluoroalkyl. In some embodiments, each $R^3$ is an independently selected $C_{1-3}$ alkyl group. In some embodiments, each $R^3$ is methyl.

In some embodiments, n is 0 or 1. In some embodiments, n is 0.

In some embodiments, the compound of Formula I, or a pharmaceutically acceptable salt thereof, is a compound of Formula VI:

or a pharmaceutically acceptable salt thereof, wherein variables $R^1$ and $R^3$ are defined according to the definitions provided herein for compounds of Formula I.

In some embodiments, $R^1$ is $C_{1-6}$ alkyl. In some embodiments, $R^1$ is $C_{1-3}$ alkyl. In some embodiments, $R^1$ is ethyl.

In some embodiments, each $R^3$ is independently selected from the group consisting of halo, $C_{1-3}$ alkyl, and $C_{1-6}$ haloalkyl. In some embodiments, each R³ is independently selected from the group consisting of halo, C₁₋₆ alkyl, and C₁₋₃ haloalkyl. In some embodiments, each R³ is independently selected from the group consisting of halo, C₁₋₃ alkyl, and C₁₋₃ haloalkyl. In some embodiments, each R³ is independently selected from the group consisting of halo, C₁₋₆ alkyl, and C₁₋₆ fluoroalkyl. In some embodiments, each R³ is independently selected from the group consisting of halo, C₁₋₃ alkyl, and C₁₋₆ fluoroalkyl. In some embodiments, each R³ is independently selected from the group consisting of halo, C₁₋₆ alkyl, and C₁₋₃ fluoroalkyl. In some embodiments, each R³ is independently selected from the group consisting of halo, C₁₋₃ alkyl, and C₁₋₃ fluoroalkyl. In some embodiments, each R³ is independently selected from the group consisting of fluoro, C₁₋₆ alkyl, and C₁₋₆ haloalkyl. In some embodiments, each R³ is independently selected from the group consisting of fluoro, C₁₋₃ alkyl, and C₁₋₆ fluoroalkyl. In some embodiments, each R³ is independently selected from the group consisting of fluoro, C₁₋₆ alkyl, and C₁₋₃ fluoroalkyl. In some embodiments, each R³ is independently selected from the group consisting of fluoro, C₁₋₃ alkyl, and C₁₋₃ fluoroalkyl. In some embodiments, each R³ is an independently selected C₁₋₃ alkyl group. In some embodiments, each R³ is methyl.

In some embodiments, the compound of Formula I is a compound of Formula VII:

or a pharmaceutically acceptable salt thereof, wherein variables R¹ and R³ are defined according to the definitions provided herein for compounds of Formula I.

In some embodiments, R¹ is $C_{1-6}$ alkyl. In some embodiments, R¹ is $C_{1-3}$ alkyl. In some embodiments, R¹ is ethyl.

In some embodiments, each R³ is independently selected from the group consisting of halo, $C_{1-3}$ alkyl, and $C_{1-6}$ haloalkyl. In some embodiments, each R³ is independently selected from the group consisting of halo, $C_{1-6}$ alkyl, and $C_{1-3}$ haloalkyl. In some embodiments, each R³ is independently selected from the group consisting of halo, $C_{1-3}$ alkyl, and $C_{1-3}$ haloalkyl. In some embodiments, each R³ is independently selected from the group consisting of halo, $C_{1-6}$ alkyl, and $C_{1-6}$ fluoroalkyl. In some embodiments, each R³ is independently selected from the group consisting of halo, $C_{1-3}$ alkyl, and $C_{1-6}$ fluoroalkyl. In some embodiments, each R³ is independently selected from the group consisting of halo, $C_{1-6}$ alkyl, and $C_{1-3}$ fluoroalkyl. In some embodiments, each R³ is independently selected from the group consisting of halo, $C_{1-3}$ alkyl, and $C_{1-3}$ fluoroalkyl. In some embodiments, each R³ is independently selected from the group consisting of fluoro, $C_{1-6}$ alkyl, and $C_{1-6}$ haloalkyl. In some embodiments, each R³ is independently selected from the group consisting of fluoro, $C_{1-3}$ alkyl, and $C_{1-6}$ fluoroalkyl. In some embodiments, each R³ is independently selected from the group consisting of fluoro, $C_{1-6}$ alkyl, and $C_{1-3}$ fluoroalkyl. In some embodiments, each R³ is independently selected from the group consisting of fluoro, $C_{1-3}$ alkyl, and $C_{1-3}$ fluoroalkyl. In some embodiments, each R³ is an independently selected $C_{1-3}$ alkyl group. In some embodiments, each R³ is methyl.

In some embodiments, the compound of Formula I is a compound of Formula VIII:

or a pharmaceutically acceptable salt thereof, wherein n is an integer from 0 to 5 and variables R¹ and R³ are defined according to the definitions provided herein for compounds of Formula I.

In some embodiments, R¹ is $C_{1-6}$ alkyl. In some embodiments, R¹ is $C_{1-3}$ alkyl. In some embodiments, R¹ is ethyl.

In some embodiments, each R³ is independently selected from the group consisting of halo, $C_{1-3}$ alkyl, and $C_{1-6}$ haloalkyl. In some embodiments, each R³ is independently selected from the group consisting of halo, $C_{1-6}$ alkyl, and $C_{1-3}$ haloalkyl. In some embodiments, each R³ is independently selected from the group consisting of halo, $C_{1-3}$ alkyl, and $C_{1-3}$ haloalkyl. In some embodiments, each R³ is independently selected from the group consisting of halo, $C_{1-6}$ alkyl, and $C_{1-6}$ fluoroalkyl. In some embodiments, each R³ is independently selected from the group consisting of halo, $C_{1-3}$ alkyl, and $C_{1-6}$ fluoroalkyl. In some embodiments, each R³ is independently selected from the group consisting of halo, $C_{1-6}$ alkyl, and $C_{1-3}$ fluoroalkyl. In some embodiments, each R³ is independently selected from the group consisting of halo, $C_{1-3}$ alkyl, and $C_{1-3}$ fluoroalkyl. In some embodiments, each R³ is independently selected from the group consisting of fluoro, $C_{1-6}$ alkyl, and $C_{1-6}$ haloalkyl. In some embodiments, each R³ is independently selected from the group consisting of fluoro, $C_{1-3}$ alkyl, and $C_{1-6}$ fluoroalkyl. In some embodiments, each R³ is independently selected from the group consisting of fluoro, $C_{1-6}$ alkyl, and $C_{1-3}$ fluoroalkyl. In some embodiments, each R³ is independently selected from the group consisting of fluoro, $C_{1-3}$ alkyl, and $C_{1-3}$ fluoroalkyl. In some embodiments, each R³ is an independently selected $C_{1-3}$ alkyl group. In some embodiments, each R³ is methyl.

In some embodiments, n is an integer from 0 to 3. In some embodiments, n is 0. In some embodiments, n is 1. In some embodiments, n is 2. In some embodiments, n is 3.

In some embodiments, the compound of Formula I is a compound of Formula X:

or a pharmaceutically acceptable salt thereof, wherein n is an integer from 0 to 5 and variables R¹ and R³ are defined according to the definitions provided herein for compounds of Formula I.

In some embodiments, R¹ is $C_{1-6}$ alkyl. In some embodiments, R¹ is $C_{1-3}$ alkyl. In some embodiments, R¹ is ethyl.

In some embodiments, each R³ is independently selected from the group consisting of halo, $C_{1-3}$ alkyl, and $C_{1-6}$ haloalkyl. In some embodiments, each R³ is independently selected from the group consisting of halo, $C_{1-6}$ alkyl, and $C_{1-3}$ haloalkyl. In some embodiments, each R³ is independently selected from the group consisting of halo, $C_{1-3}$ alkyl, and $C_{1-3}$ haloalkyl. In some embodiments, each $R^3$ is independently selected from the group consisting of halo, $C_{1-6}$ alkyl, and $C_{1-6}$ fluoroalkyl. In some embodiments, each $R^3$ is independently selected from the group consisting of halo, $C_{1-3}$ alkyl, and $C_{1-6}$ fluoroalkyl. In some embodiments, each $R^3$ is independently selected from the group consisting of halo, $C_{1-6}$ alkyl, and $C_{1-3}$ fluoroalkyl. In some embodiments, each $R^3$ is independently selected from the group consisting of halo, $C_{1-3}$ alkyl, and $C_{1-3}$ fluoroalkyl. In some embodiments, each $R^3$ is independently selected from the group consisting of fluoro, $C_{1-6}$ alkyl, and $C_{1-6}$ haloalkyl. In some embodiments, each $R^3$ is independently selected from the group consisting of fluoro, $C_{1-3}$ alkyl, and $C_{1-6}$ fluoroalkyl. In some embodiments, each $R^3$ is independently selected from the group consisting of fluoro, $C_{1-6}$ alkyl, and $C_{1-3}$ fluoroalkyl. In some embodiments, each $R^3$ is independently selected from the group consisting of fluoro, $C_{1-3}$ alkyl, and $C_{1-3}$ fluoroalkyl. In some embodiments, each $R^3$ is an independently selected $C_{1-3}$ alkyl group. In some embodiments, each $R^3$ is methyl.

In some embodiments, n is an integer from 0 to 3. In some embodiments, n is 0. In some embodiments, n is 1. In some embodiments, n is 2. In some embodiments, n is 3.

In some embodiments, the compound provided herein is selected from the group consisting of:

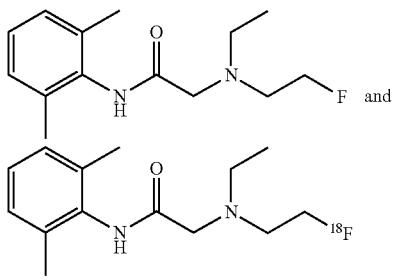

or a pharmaceutically acceptable salt thereof.

In some embodiments, the compound provided herein is:

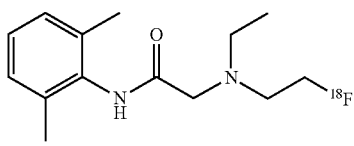 [SMILES: CCN(CC[18F])CC(=O)Nc1c(C)cccc1C]

or a pharmaceutically acceptable salt thereof.

In some embodiments, the compound provided herein (e.g., a compound of any of Formulas I-VIII and X), or a pharmaceutically acceptable salt thereof, comprises at least one halo or $C_{1-6}$ haloalkyl group. In some embodiments, the compound, or pharmaceutically acceptable salt thereof, comprises at least one halo group. In some embodiments, the compound, or a pharmaceutically acceptable salt thereof, comprises at least one fluoro group. In some embodiments, the compound, or a pharmaceutically acceptable salt thereof, comprises at least one $^{18}$F group. In some embodiments, the compound, or a pharmaceutically acceptable salt thereof, comprises at least one $C_{1-6}$ haloalkyl group. In some embodiments, the compound, or a pharmaceutically acceptable salt thereof, comprises at least one $C_{1-6}$ fluoroalkyl group. In some embodiments, the compound, or a pharmaceutically acceptable salt thereof, comprises at least one $C_{1-6}$ ($^{18}$fluoro)alkyl group.

Unless specifically defined, compounds and salts provided herein can also include all isotopes of atoms occurring in the intermediates or final compounds. Isotopes include those atoms having the same atomic number but different mass numbers.

Accordingly, the present application further provides radiolabeled compounds (e.g., a compound of Formula VII or X, or a radiolabeled compound of any of Formulas I-VI or VIII), or pharmaceutically acceptable salts thereof, that would be useful not only in imaging techniques but also in assays, both in vitro and in vivo, for identifying (e.g., locating, labeling), measuring (e.g., quantitative or non-quantitative measuring) and quantitating voltage gated sodium channel levels in cell samples, tissue samples, and subjects provided herein.

In some embodiments, a compound provided herein (e.g., a compound of any of Formulas I-VIII and X) or pharmaceutically acceptable salt, comprises at least one radioisotope. As used herein, the term "radioisotope" refers to an atom having an atomic mass or mass number different from the atomic mass or mass number typically found in nature (i.e., naturally occurring). A "radiolabeled" compound is a compound provided herein where one or more atoms are replaced or substituted by an atom having an atomic mass or mass number different from the atomic mass or mass number typically found in nature (i.e., naturally occurring). Example radioisotopes include, but are not limited to, $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{67}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{99m}$Tc, $^{110m}$In, $^{111}$In, $^{118}$Sb, $^{120}$I, $^{121}$I, $^{122}$I, $^{123}$I, $^{124}$I, $^{124}$I, $^{131}$I, and $^{201}$Tl.

In some embodiments, the radioisotope is a positron emitter. As used herein the term "positron emitter" refers to a radioisotope wherein a proton is converted to a neutron, thereby releasing a positron and an electron neutrino. In some embodiments, the positron emitter is $^{11}$C or $^{18}$F.

In some embodiments, the compound or pharmaceutically acceptable salt provided herein comprises at least one radioisotope selected from the group consisting of $^{11}$C, $^{13}$N, and $^{18}$F. In some embodiments, the compound or pharmaceutically acceptable salt comprises at least one $^{18}$F radioisotope. In some embodiments, at least one halo group of a compound provided herein is a radioisotope. In some embodiments at least one halo group of a compound provided herein is $^{18}$F. In some embodiments, at least one haloalkyl or fluoroalkyl group of a compound provided herein comprises at least one radioisotope. In some embodiments, at least one haloalkyl or fluoroalkyl group of a compound provided herein comprises at least one $^{18}$F radioisotope.

In some embodiments, $R^N$ comprises at least one radioisotope. In some embodiments, $R^N$ comprises one radioisotope. In some embodiments, $R^N$ comprises one $^{18}$F radioisotope.

In some embodiments, $R^1$ comprises at least one radioisotope. In some embodiments, $R^1$ comprises one radioisotope. In some embodiments, $R^1$ comprises one $^{18}$F radioisotope.

In some embodiments, $R^2$ comprises at least one radioisotope. In some embodiments, $R^2$ comprises one radioisotope. In some embodiments, $R^2$ comprises one $^{18}$F radioisotope.

In some embodiments, at least one $R^3$ group comprises at least one radioisotope. In some embodiments, at least one $R^3$ group comprises one radioisotope. In some embodiments, at least one $R^3$ group comprises one $^{18}F$ radioisotope.

Unless otherwise stated, when an atom is designated as an isotope or radioisotope (e.g., deuterium, $^{11}C$, $^{18}F$), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

As used herein, the term "Ci", refers to "Curie", a unit of radioactivity.

As used herein, the term "specific activity" refers to the activity of a given radioisotope per unit mass, for example, Ci/g.

Synthesis

As will be appreciated, the compounds provided herein, including salts thereof, can be prepared using known organic synthesis techniques and can be synthesized according to any of numerous possible synthetic routes.

The compounds provided herein can be prepared, for example, according to the procedure shown in Scheme 1, wherein groups $R^1$, $R^2$, $R^3$, and n are as defined herein for compounds of Formula I. For example, reacting compound (i) with an appropriately substituted compound (ii), where LG is a leaving group (e.g., a tosylate group, a mesylate group, and the like) at elevated temperature in the presence of a base (e.g. potassium carbonate) affords a compound of Formula I (e.g. a compound of Formula Ia).

Scheme 1.

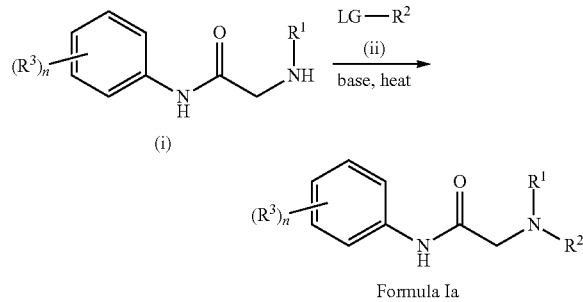

Formula Ia

The compounds provided herein can also be prepared, for example, according to the procedure shown in Scheme 2, wherein groups $R^1$, $R^2$, $R^3$, and n are as defined herein for compounds of Formula I. For example, reacting compound (iii) with an appropriately substituted compound (iv), where LG is a leaving group (e.g., a tosylate group, a mesylate group, and the like) at elevated temperature in the presence of a base (e.g. potassium carbonate) affords a compound of Formula I (e.g., a compound of Formula Ia).

Scheme 2.

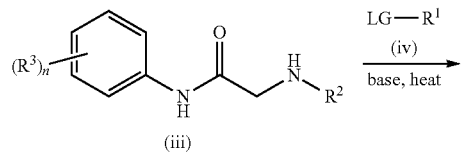

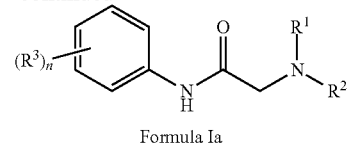

Formula Ia

The radiolabeled compounds of Formula I, or pharmaceutically acceptable salts thereof, may be prepared, for example, according to the procedure shown in Scheme 3, wherein groups $R^1$, $R^3$, and n are as defined herein for compounds of Formula I, and $R^{2*}$ is a group comprising at least one radioisotope. For example, reacting compound (v) with an appropriately substituted compound (vi), where LG is a leaving group (e.g., a tosylate group, a mesylate group, and the like) at elevated temperature in the presence of a base (e.g. potassium carbonate) affords a radiolabeled compound of Formula I (e.g., a radiolabeled compound of Formula Ia).

Scheme 3.

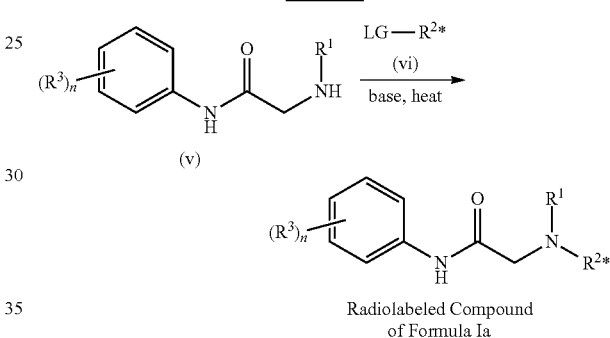

Radiolabeled Compound
of Formula Ia

The radiolabeled compounds of Formula I, or pharmaceutically acceptable salts thereof, may be also prepared, for example, according to the procedure shown in Scheme 4, wherein groups $R^2$, $R^3$, and n are as defined herein for compounds of Formula I, and $R^{1*}$ is a group comprising at least one radioisotope. For example, reacting compound (vii) with an appropriately substituted compound (viii), where LG is a leaving group (e.g., a tosylate group, a mesylate group, and the like) at elevated temperature in the presence of a base (e.g. potassium carbonate) affords a radiolabeled compound of Formula I (e.g., a radiolabeled compound of Formula Ia).

Scheme 4.

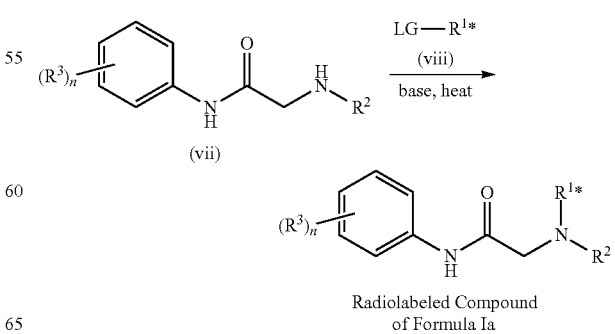

Radiolabeled Compound
of Formula Ia

Additional synthetic methods for incorporating radioisotopes into organic compounds are well known in the art, and one of ordinary skill in the art will readily recognize other methods applicable for preparing the radiolabeled compounds and salts provided herein.

The present application further provides a method of preparing a compound of Formula VIII:

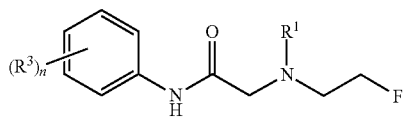

or a salt thereof, comprising reacting a compound of Formula Ic:

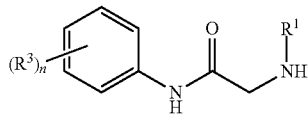

with a compound of Formula IX:

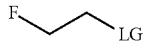

in the presence of a base, wherein LG is a leaving group and variables n, $R^1$, and $R^3$ are defined according to the definitions provided herein for compounds of Formula I.

In some embodiments, the base is a carbonate base. Example carbonate bases include, but are not limited to, lithium carbonate, sodium carbonate, potassium carbonate, ammonium carbonate, the like. In some embodiments, the base is potassium carbonate.

In some embodiments, the reacting is performed at a temperature of about 50° C. to about 150° C., for example, about 50° C. to about 150° C., about 50° C. to about 130° C., about 50° C. to about 110° C., about 50° C. to about 90° C., about 50° C. to about 70° C., about 70° C. to about 150° C., about 70° C. to about 130° C., about 70° C. to about 110° C., about 70° C. to about 90° C., about 90° C. to about 150° C., about 90° C. to about 130° C., about 90° C. to about 110° C., about 110° C. to about 150° C., about 110° C. to about 130° C., or about 110° C. to about 130° C. In some embodiments, the reacting is performed at a temperature of about 90° C. to about 110° C. In some embodiments, about 1 to about 5 equivalents of the compound of Formula IX is used based on 1 equivalent of the compound of Formula Ic, for example, about 1 to about equivalents, about 1 to about 4 equivalents, about 1 to about 3 equivalents, about 1 to about 2 equivalents, about 1 to about 1.5 equivalents, about 1.5 to about 5 equivalents, about 1.5 to about 4 equivalents, about 1.5 to about 3 equivalents, about 1.5 to about 2 equivalents, about 2 to about 5 equivalents, about 2 to about 4 equivalents, about 2 to about 3 equivalents, about 3 to about 5 equivalents, about 3 to about 4 equivalents, or about 4 to about 5 equivalents. In some embodiments, about 1 to about 1.5 equivalents of the compound of Formula IX is used based on 1 equivalent of the compound of Formula Ic.

The present application further provides a process of preparing a compound of Formula X:

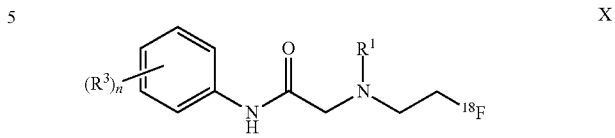

or a salt thereof, comprising reacting a compound of Formula Ic:

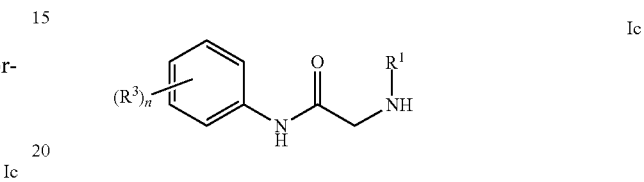

with a compound of Formula IXa:

wherein LG is a leaving group and variables n, $R^1$, and $R^3$ are defined according to the definitions provided herein for compounds of Formula I.

In some embodiments, the reacting is performed at a temperature of about 50° C. to about 150° C., for example, about 50° C. to about 150° C., about 50° C. to about 130° C., about 50° C. to about 110° C., about 50° C. to about 90° C., about 50° C. to about 70° C., about 70° C. to about 150° C., about 70° C. to about 130° C., about 70° C. to about 110° C., about 70° C. to about 90° C., about 90° C. to about 150° C., about 90° C. to about 130° C., about 90° C. to about 110° C., about 110° C. to about 150° C., about 110° C. to about 130° C., or about 110° C. to about 130° C. In some embodiments, the reacting is performed at a temperature of about 90° C. to about 110° C.

As used herein, the term "leaving group" is understood in the art and refers to a molecular fragment of a compound which, upon reaction of the compound with an appropriate reactant, undergoes heterolytic bond cleavage. In some embodiments, the leaving group is an anionic leaving group (i.e., the molecular fragment generated upon the heterolytic bond cleavage is an anionic group). Example anionic leaving groups include, but are not limited to, but are not limited to, halides (e.g., chloride, bromide, iodide), sulfonate esters (e.g., tosylate or mesylate). In some embodiments, the leaving group is a neutral leaving group (i.e., the molecular fragment generated upon the heterolytic bond cleavage is a neutral group). Example neutral leaving groups include, but are not limited to, water and ammonia. In some embodiments, LG is a leaving group selected from the group consisting of tosylate and mesylate. In some embodiments, LG is a tosylate group.

In some embodiments, the reacting is performed in a solvent. In some embodiments, the solvent is a polar aprotic solvent or a polar protic solvent. Example polar aprotic solvents include, but are not limited to, tetrahydrofuran, ethyl acetate, acetone, dimethylformamide, acetonitrile, and dimethyl sulfoxide. In some embodiments, the solvent is selected from the group consisting of dimethylformamide and acetonitrile. In some embodiments, the solvent is a polar protic solvent. Example polar protic solvents include, but are not limited to, alcohol solvents (e.g., methanol, ethanol, iso-propanol, butanol, and the like), nitromethane, and water.

The present application further provides a process of preparing a compound of the following formula:

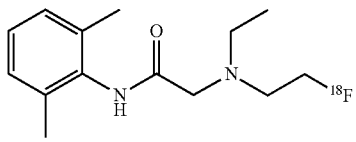 [SMILES: CCN(CC[18F])CC(=O)Nc1c(C)cccc1C]

or a salt thereof, comprising reacting N-(2,6-dimethylphenyl)-2-(ethylamino)acetamide with 2-(fluoro-$^{18}$F)ethyl 4-methylbenzenesulfonate, wherein the reacting is performed in a polar aprotic solvent. In some embodiments, the solvent is selected from the group consisting of dimethylformamide and acetonitrile.

In some embodiments, the process further comprises preparing the compound of Formula IXa:

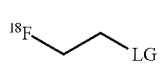

IXa by reacting an $^{18}$F-salt with a compound of Formula XII:

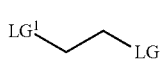

XII in the presence of a solvent, wherein LG and LG$^1$ are independently selected leaving groups. In some embodiments, LG and LG$^1$ are the same leaving group. In some embodiments, LG and LG$^1$ are different leaving groups.

In some embodiments, the compound of Formula IXa is 2-(fluoro-$^{18}$F)ethyl 4-methylbenzenesulfonate. In some embodiments, the compound of Formula XII is ethane-1,2-diyl bis(4-methylbenzenesulfonate). In some embodiments, the $^{18}$F-salt is $^{18}$FK. In some embodiments, the solvent is a polar aprotic solvent. In some embodiments, the solvent is acetonitrile.

In some embodiments, the process is performed at a temperature of about 50° C. to about 150° C., for example, about 50° C. to about 150° C., about 50° C. to about 130° C., about 50° C. to about 110° C., about 50° C. to about 90° C., about 50° C. to about 70° C., about 70° C. to about 150° C., about 70° C. to about 130° C., about 70° C. to about 110° C., about 70° C. to about 90° C., about 90° C. to about 150° C., about 90° C. to about 130° C., about 90° C. to about 110° C., about 110° C. to about 150° C., about 110° C. to about 130° C., or about 110° C. to about 130° C. In some embodiments, the reacting is performed at a temperature of about 100° C. to about 120° C. In some embodiments, the processes provided herein may be performed as a one-pot synthesis.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry*: Reactions, *Mechanisms, and Structure*, 6$^{th}$ Ed. (Wiley, 2007); Trost et al. (Ed.), *Comprehensive Organic Synthesis* (Pergamon Press, 1991).

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$-includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1}$-4, $C_{1-6}$, and the like.

As used herein, the term "$C_{n-m}$ alkylene", employed alone or in combination with other terms, refers to a divalent alkyl linking group having n to m carbons. Examples of alkylene groups include, but are not limited to, methylene, ethan-1,2-diyl, propan-1,3-diyl, propan-1,2-diyl, and the like. In some embodiments, the alkylene moiety contains 1 to 6, 1 to 3, or 1 to 2 carbon atoms.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "halo" refers to F, Cl, Br, or I. In some embodiments, the halo is F, Cl, or Br. In some embodiments, the halo is F. In some embodiments, the halo is $^{18}$F.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only (e.g, a $C_{1-6}$ fluoroalkyl group). In some embodiments, the alkyl group has 1 to 6, 1 to 4, or 1 to 3 carbon atoms. In some embodiments, the haloalkyl group comprises one or more $^{18}$F radioisotope. In some embodiments, the haloalkyl group comprises one $^{18}$F radioisotope.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons (i.e., a $C_{3-10}$ cycloalkyl group). Ring-forming carbon atoms of a cycloalkyl group can be optionally substituted by oxo or sulfido (e.g., C(=O) or C(=S)). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, and the like. In some embodiments, cycloalkyl is cyclopropyl, cyclobutyl, cyclopentyl, cyclohexyl, cycloheptyl, cyclooctyl, cyclononyl, or adamantyl. In some embodiments, the cycloalkyl has 6-10 ring-forming carbon atoms (i.e., a $C_{6-10}$ cycloalkyl group). In some embodiments, the cycloalkyl has 3-6 ring-forming carbon atoms (i.e., a $C_{3-6}$ cycloalkyl group).

As used herein, the term "heteroaryl" refers to a monocyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, the heteroaryl ring has 1, 2, 3, or 4 heteroatom ring members independently selected from nitrogen and sulfur. In some embodiments, any ring-forming N in a heteroaryl moiety can form an N-oxide. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen and sulfur. In some embodiments, the heteroaryl has 5-6 ring atoms and 1 or 2 heteroatom ring members independently selected from nitrogen and sulfur. Exemplary five-membered ring heteroaryls include, but are not limited to, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. Exemplary six-membered ring heteroaryls include, but are not limited to, pyridyl, pyrazinyl, pyrimidinyl, triazinyl and pyridazinyl.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term, "room temperature" or "RT" as used herein, are understood in the art, and refer generally to a temperature (e.g., a reaction temperature) that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use,* Wiley-VCH, 2002.

Methods of Use

The present application further provides of a method of blocking one or more isoforms of voltage gated sodium channels in a cell sample or tissue sample. In some embodiments, the method comprises comprising contacting the cell sample or tissue sample with a compound provided herein (e.g., a compound of any of Formulas I-VIII and X), or a pharmaceutically acceptable salt thereof.

The present application further provides a method of blocking one or more isoforms of voltage gated sodium channels in a subject. As used herein, the term "subject," refers to any animal, including mammals. Example subjects include, but are not limited to, mice, rats, rabbits, dogs, cats, swine, cattle, sheep, horses, primates, and humans. In some embodiments, the subject is a human. In some embodiments, the method comprises administering to the subject a therapeutically effective amount of a compound provided herein (e.g., a compound of any of Formulas I-VIII and X), or a pharmaceutically acceptable salt thereof.

In some embodiments, the method comprises blocking one or more voltage gated sodium channel isoforms selected from the group consisting of Nav1.1, Nav1.2, Nav1.3, Nav1.4, Nav1.5, Nav1.6, Nav1.7, Nav1.8, Nav1.9, and $Na_X$. In some embodiments, the method comprises blocking voltage gated sodium channel Nav1.5. As used herein, the term "blocking" refers to the binding and occluding of an intracellular or extracellular pore opening of one or more voltage gated sodium channels, thereby causing decreased conductivity of sodium ions through the voltage gated sodium channel compared to a voltage gated sodium channel that is not blocked.

The present application further provides a method of imaging one or more voltage gated sodium channel isoforms in a cell sample or tissue sample.

In some embodiments, the method comprises:
i) contacting the cell sample of tissue sample with compound which binds to one or more voltage gated sodium channel isoforms; and
ii) imaging the cell sample or tissue sample with an imaging technique.

In some embodiments, the method comprises:
i) contacting the cell sample or tissue sample with a compound provided herein (e.g., a compound of any of Formulas I-VIII and X), or a pharmaceutically acceptable salt thereof; and
ii) imaging the cell sample or tissue sample with an imaging technique.

The present application further provides a method of imaging one or more voltage gated sodium channel isoforms in a subject.

In some embodiments, the method comprises:
i) administering to the subject a compound which binds to one or more voltage gated sodium channel isoforms; and
ii) imaging the subject with an imaging technique.

In some embodiments, the method comprises:
i) administering to the subject a compound provided herein (e.g., a compound of any of Formulas I-VIII and X), or a pharmaceutically acceptable salt thereof; and
ii) imaging the subject with an imaging technique.

In some embodiments, the method is a method of imaging one or more voltage gated sodium channel isoforms. In some embodiments, the method comprises imaging one or more voltage gated sodium channel isoforms selected from the group consisting of Nav1.1, Nav1.2, Nav1.3, Nav1.4, Nav1.5, Nav1.6, Nav1.7, Nav1.8, Nav1.9, and $Na_X$. In some embodiments, the method comprises imaging voltage gated sodium channel Nav1.5. In some embodiments, the voltage gated sodium channel isoform is selected from the group consisting of SCN1A, SCN2A, SCN3A, SCN4A, SCN5A, SCN7A, SCN8A, SCN9A, SCN10A, and SCN11A. In some embodiments, the voltage gated sodium channel isoform is SCN5A.

The present application further provides a method of imaging the heart in a subject. The present application further provides a method of imaging the spinal cord in a subject. The present application further provides a method of imaging a tumor in a subject.

In some embodiments, the method comprises:
i) administering to the subject a compound which binds to one or more voltage gated sodium channel isoforms; and
ii) imaging the subject with an imaging technique.

In some embodiments, the method comprises:
i) administering to the subject a compound provided herein (e.g., a compound of any of Formulas I-VIII and X), or a pharmaceutically acceptable salt thereof; and
ii) imaging the subject with an imaging technique.

In some embodiments, the method further comprises optionally administering an imaging agent prior to the imaging of step ii). In some embodiments, the compound which binds to one or more voltage gated sodium channel isoforms comprises one or more imaging agents (e.g., a fluorescent moiety or a radioisotope capable of being imaged with an imaging technique). In some embodiments, the compound provided herein (e.g., a compound of any of Formulas I-VIII and X), or a pharmaceutically acceptable salt thereof, comprises one or more imaging agents (e.g., a fluorescent moiety or a radioisotope capable of being imaged with an imaging technique). In some embodiments, the compound, or pharmaceutically acceptable salt, provided herein is a radiolabeled compound (e.g. a radiolabeled compound of any of Formulas I-VIII and X), or a pharmaceutically acceptable salt thereof.

The present application further provides a method of monitoring treatment of a disease associated with reduced total expression levels of one or more voltage gated sodium channel isoforms in a subject. The present application further provides a method of monitoring treatment of a disease associated with increased total expression levels of one or more voltage gated sodium channel isoforms in a subject. The present application further provides a method of monitoring treatment of a disease associated with increased functional activity (i.e. opening frequency) of one or more voltage gated sodium channel isoforms in a subject. The present application further provides a method of imaging a disease associated with reduced or increased expression levels of one or more voltage gated sodium channel isoforms in a subject. The present application further provides a method of imaging a disease associated with increased functional activity (i.e. opening frequency) of one or more voltage gated sodium channel isoforms in a subject.

In some embodiments, the method comprises:
i) imaging the subject with an imaging technique;
ii) administering to the subject a compound which binds to one or more voltage gated sodium channel isoforms;
iii) imaging the subject with an imaging technique; and
iv) comparing the image of step i) and the image of step iii).

In some embodiments, the method comprises:
i) imaging the subject with an imaging technique;
ii) administering to the subject a compound provided herein (e.g., a compound of any of Formulas I-VIII and X), or a pharmaceutically acceptable salt thereof;
iii) imaging the subject with an imaging technique; and
iv) comparing the image of step i) and the image of step iii).

In some embodiments, the method is a method of monitoring treatment of a disease associated with abnormal expression levels of one or more voltage gated sodium channel isoforms in a subject. In some embodiments, the method is a method of imaging a disease associated with abnormal expression levels of one or more voltage gated sodium channel isoforms in a subject. In some embodiments, the method is a method of monitoring treatment of a disease associated with abnormal activity of one or more voltage gated sodium channel isoforms in a subject. In some embodiments, the method is a method of imaging a disease associated with abnormal activity of one or more voltage gated sodium channel isoforms in a subject.

In some embodiments, the disease is associated with abnormal expression levels or activity of one or more voltage gated sodium channel isoforms selected from the group consisting of Nav1.1, Nav1.2, Nav1.3, Nav1.4, Nav1.5, Nav1.6, Nav1.7, Nav1.8, Nav1.9, and $Na_x$. In some embodiments, the disease is associated with abnormal expression levels or activity of voltage gated sodium channel Nav1.5. In some embodiments, the disease is associated with low expression levels of voltage gated sodium channel Nav1.5 in the subject compared to the levels of sodium channel Nav1.5 in a control subject. In some embodiments, the disease is associated with abnormal activity of voltage gated sodium channel Nav1.5 in the subject compared to the activity of sodium channel Nav1.5 in a control subject.

In some embodiments, the disease is associated with abnormal expression levels or single channel activity of voltage gated sodium channel isoform SCN5A. In some embodiments, the disease is associated with low expression levels of voltage gated sodium channel isoform SCN5A in the subject compared to the expression levels of sodium channel isoform SCN5A in a control subject. In some embodiments, the disease is associated with abnormal activity of voltage gated sodium channel isoform SCN5A in the subject compared to the activity of sodium channel isoform SCN5A in a control subject.

In some embodiments, the disease is selected from the group consisting of cardiovascular disease, neurological disease, and cancer.

In some embodiments, the cardiovascular disease is selected from the group consisting of cardiomyopathy (e.g. dilated cardiomyopathy), ventricular fibrillation, tachycardia, myocardial infarction, long QT syndrome, Brugada syndrome, progressive cardiac conduction disease, sick sinus syndrome, atrial fibrillation, hypertension, myocarditis, and heart failure. In some embodiments, the cardiovascular disease comprises cardiac arrhythmia.

In some embodiments, the neurological disease is selected from the group consisting of multiple sclerosis and amyotrophic lateral sclerosis, neuropathic pain, diabetic pain, cancer pain, trigeminal neuralgia.

In some embodiments, the cancer is selected from the group consisting of breast cancer, prostate cancer, and small cell lung cancer, and non-small cell lung cancer.

The present application further provides a method of determining the risk of cardiovascular disease in a subject. In some embodiments, the cardiovascular disease is selected from the group consisting of cardiomyopathy (e.g. dilated cardiomyopathy), ventricular fibrillation, tachycardia, myocardial infarction, long QT syndrome, Brugada syndrome, progressive cardiac conduction disease, sick sinus syndrome, atrial fibrillation, hypertension, myocarditis, and heart failure. In some embodiments, the cardiovascular disease is heart failure.

In some embodiments, the method comprises:
i) administering to the subject a compound which binds to one or more voltage gated sodium channel isoforms; and
ii) imaging the subject with an imaging technique; In some embodiments, the method comprises:
i) administering to the subject a compound provided herein (e.g., a compound of any of Formulas I-VIII and X), or a pharmaceutically acceptable salt thereof;
ii) imaging the subject with an imaging technique;

In some embodiments, the method further comprises comparing the image of step ii) to a database of images, wherein the database comprises images selected from the group consisting of images of the heart of one or more healthy subjects, images of the heart of one or more control subjects, images of the heart of one or more subjects determined to have about 10% to 90% risk of developing cardiovascular disease or symptoms associated with cardiovascular disease, for example, about 10% to 90% risk, about 10% to 75% risk, about 10% to 50% risk, about 10% to 40% risk, about 10% to 25% risk, about 25% to 90% risk, about 25% to 75% risk, about 25% to 50% risk, about 25% to 40% risk, about 40% to 90% risk, about 40% to 75% risk, about 40% to 50% risk, about 50% to 90% risk, about 50% to 75% risk, about 75% to 90% risk, images of the heart of one or more subjects determined to have a greater than about 5% risk of developing cardiovascular disease or symptoms associated with cardiovascular disease, images of the heart of one or more subjects determined to have a greater than about 10% risk of developing cardiovascular disease or symptoms associated with cardiovascular disease, images of the heart of one or more subjects determined to have a greater than about 20% risk of developing cardiovascular disease or symptoms associated with cardiovascular disease, images of the heart of one or more subjects determined to have a greater than about 30% risk of developing cardiovascular disease or symptoms associated with cardiovascular disease, images of the heart of one or more subjects determined to have a greater than about 40% risk of developing cardiovascular disease or symptoms associated with cardiovascular disease, images of the heart of one or more subjects determined to have a greater than about 50% risk of developing cardiovascular disease or symptoms associated with cardiovascular disease, images of the heart of one or more subjects determined to have a greater than about 60% risk of developing cardiovascular disease or symptoms associated with cardiovascular disease, images of the heart of one or more subjects determined to have a greater than about 70% risk of developing cardiovascular disease or symptoms associated with cardiovascular disease, images of the heart of one or more subjects determined to have a greater than about 80% risk of developing cardiovascular disease or symptoms associated with cardiovascular disease, images of the heart of one or more subjects determined to have a greater than about 90% risk of developing cardiovascular disease or symptoms associated with cardiovascular disease, images of the heart of one or more subjects determined to have a greater than about 95% risk of developing cardiovascular disease or symptoms associated with cardiovascular disease, or any combination thereof.

Example compounds which bind to one or more voltage gated sodium channel isoforms include, but are not limited to, Class 1a antiarrhythmic agents (e.g., quinidine, ajmaline, procainamide, and disopyramide); Class 1b antiarrhythmic agents (e.g., lidocaine, phenytoin, mexiletine, and tocainide), and Class 1c antiarrhythmic agents (e.g., encainide, flecainide, propafenone, moricizine, and fomocaine). In some embodiments, the compound is a Class 1b antiarrhythmic agent. In some embodiments, the compound is selected from the group consisting of lidocaine and mexiletine.

In some embodiments, a "normal", "healthy", or "control" subject may be determined using an age-matched control, age-matched controls, or age-matched binning. As used herein, the term "age-matched control" and "age-matched controls" refers to a subject or subjects within about 6.5 years in age compared to a test subject (e.g., +6.5 or −6.5 years). In some embodiments, a normal or healthy subject may be determined using age-matched binning, for example, a subject or subjects ranging from about from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 40 to about 45 years old, from about 20 to about 30 years old, from about 30 to about 40 years old, from about 40 to about 50 years old, from about 50 to about 60 years old, and the like.

In some embodiments, the imaging technique is a non-invasive imaging technique. In some embodiments, the imaging technique is a minimally invasive imaging technique. As used herein, the term "minimally invasive imaging technique" comprises imaging techniques employing the use of an internal probe or injection of a compound (e.g. a radiolabeled compound) via syringe.

Example imaging techniques include, but are not limited to, magnetic resonance imaging (MRI), ultrasound imaging, tomographic imaging, positron emission tomography imaging, computed tomography, positron emission tomography with computed tomography imaging, and positron emission tomography with magnetic resonance imaging.

In some embodiments, the imaging technique is selected from the group consisting of single-photon emission computed tomography, positron emission tomography imaging, positron emission tomography with computed tomography imaging, positron emission tomography with magnetic resonance imaging. In some embodiments, the imaging technique is positron emission tomography imaging.

In some embodiments, the compound which binds to one or more voltage gated sodium channel isoforms, or the compounds provided herein (e.g., a compound of any of Formulas I-VIII and X), or pharmaceutically acceptable salts thereof, are administered to the subject in a therapeutically effective amount. As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

One or more additional therapeutic agents such as, for example, anti-inflammatory agents, steroids, immunosuppressants, anesthetics (e.g., for use in combination with a surgical procedure) or other agents useful for treating cardiovascular diseases can be used in combination with the compounds and salts provided herein.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example steroids include, but are not limited to, corticosteroids such as cortisone, dexamethasone, hydrocortisone, methylprednisolone, prednisolone, and prednisone.

Example immunosuppressants include, but are not limited to, azathioprine, chlorambucil, cyclophosphamide, cyclosporine, daclizumab, infliximab, methotrexate, and tacrolimus.

Example anesthetics include, but are not limited, to local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

Examples of agents useful for treating cardiovascular diseases include, but are not limited to, angiotensin-converting enzyme (ACE) inhibitors (e.g., enalapril, captopril), angiotensin II receptor blockers (e.g., losartan, valsartan), beta blockers (e.g., carvedilol, metoprolol, bisoprolol), calcium channel blockers (e.g., dihydropyridine agents such as amlodipine and phenylalkylamine agents such as verapamil), diuretics (e.g., furosemide), and aldosterone antagonists (e.g., spironolactone, eplerenone).

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein. In some embodiments, the compound or salt provided herein is administered during a surgical procedure. In some embodiments, the compound or salt provided herein is administered in combination with an additional therapeutic agent during a surgical procedure.

Pharmaceutical Formulations and Formulations

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds, salts, and pharmaceutical compositions provided herein are suitable for parenteral administration. In some embodiments, the compounds, salts, and pharmaceutical compositions provided herein are suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active ingredient can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

General Materials and Methods

Analytical HPLC

Solid phase: Agilent Eclipse XDB-$C_{18}$ (5 μm 4.6×150 mm); Mobile phase: A=0.1% TFA in water; B=0.1% TFA in MeCN; Gradient: 0-1 min (5% B), 1-5 min (5-50% B), 5-6 min (50% B), 6-10 min (50-95% B); Flow: 1.5 mL/min.

Semipreparative HPLC

Solid phase: Phenomenex Luna 5u C8(2) (100A 10×250 mm); Mobile Phase: 8% EtOH (200 proof) in water+0.01% phosphoric acid; Flow: 4.0 mL/min.

Radiotracer Formulations

The radiolabeled compound of Example 2 isolated from semipreparative HPLC (typically 4-6 mL) was diluted with a 1/10 volume of 10×PBS buffer and filtered through a sterile 22 μm filter into a 10 mL sterile injection vial. This injectable stock solution was diluted with sterile saline to adjust for the desired volume and amount of radioactivity. Typically, concentrations of 1 mCi/mL and volumes of 1 mL/kg were injected in rats (e.g., 0.5 mCi in 0.5 mL for a 500 g animal). For non-human primate imaging, doses of ~5 mCi were injected in volumes of 4-6 mL.

Example 1. N-(2,6-dimethylphenyl)-2-(ethyl(2-fluoroethyl)amino)acetamide

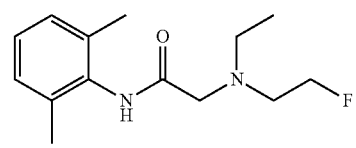 [SMILES: CCN(CCF)CC(=O)Nc1c(C)cccc1C]

N-(2,6-dimethylphenyl)-2-(ethylamino)acetamide (500 mg, 2.4 mmol, 1.0 eq) was dissolved in 5 mL DMF, and fluoroethyltosylate (635 mg, 2.9 mmol, 1.2 eq) was added, followed by potassium carbonate (440 mg, 5 mmol, 2.1 eq). The resulting suspension was stirred at 90° C. for 3 hours. After cooling to room temperature, the reaction mixture was diluted with 100 mL ethyl acetate and washed with 25 mL 1M NaOH (aq, 1×) and 25 mL of 1:1 mixture of brine and 1M NaOH (aq, 3×). The organic layer was dried using sodium sulfate and concentrated using rotary evaporation to yield an oily residue. The crude residue was purified using automated flash chromatography (ISCO, 24 g silica column, gradient 0-5% MeOH in dichloromethane) yielding the title product (335 mg, 1.3 mmol, 56% yield). The purified N-(2,6-dimethylphenyl)-2-(ethyl(2-fluoroethyl)amino)acetamide was isolated as an oil, which solidified to an off-white solid upon storage at room temperature.

TLC (silica, 5% MeOH/DCM, UV): single spot, Rf=0.41. Analytical HPLC: $R_f$=4.60 min. LRMS (LCMS, ESI): single peak, (M+H$^+$)(calc)=253.2; (M+H$^+$)(found)=253.2. HRMS (ESI): (M+H$^+$)(calc)=253.1711; (M+H$^+$)(found)=253.1743. $^{13}$C-NMR (125 MHz, acetonitrile-d$_3$, chemical shift in ppm): 135.65; 134.72; 127.84; 126.89; 82.03 (d, $^1$J=164 Hz); 57.25; 54.32 (d, $^2$J=20 Hz); 49.64; 17.73; 11.24.

Example 2. N-(2,6-dimethylphenyl)-2-(ethyl(2-(fluoro-$^{18}$F)ethyl)amino)acetamide

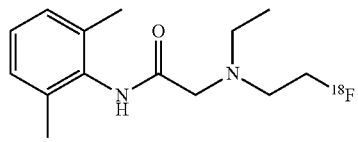 [SMILES: CCN(CC[18F])CC(=O)Nc1c(C)cccc1C]

Step 1. 2-(fluoro-$^{18}$F)ethyl 4-methylbenzenesulfonate

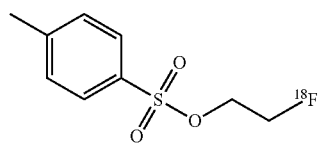

Figure 1B:
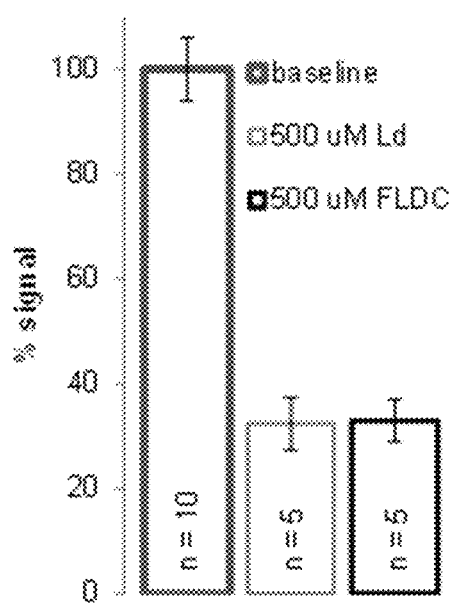
FIG. 1B shows a comparison of the known SCN5A blocker lidocaine and N-(2,6-dimethylphenyl)-2-(ethyl(2-fluoroethyl)amino)acetamide as competition ligands at the same concentration. Both ligands showed the same level of non-displaceable binding.

Ethane-1,2-diyl bis(4-methylbenzenesulfonate) (5 mg) was reacted with freshly dried $^{18}$FK[2.2.2] in 1 mL MeCN for 10 min at 110° C. The reaction mixture was added to a shielded 24 mL syringe with 20 mL of water, and a precipitate formed. This precipitate was filtered (22 μm filter) and the desired product was trapped on a strataX reversed phase cartridge, as shown in FIG. 1E. The column was dried with air using a fresh 24 mL syringe and eluted in 500 μL MeCN to afford the title compound in 40-60% non-decay corrected isolated yield.

Step 2. N-(2,6-dimethylphenyl)-2-(ethyl(2-(fluoro-$^{18}$F)ethyl)amino)acetamide Freshly prepared 2-(fluoro-$^{18}$F)ethyl 4-methylbenzenesulfonate was dissolved in 500 μL MeCN and added to a vial containing 2 mg of N-(2,6-dimethylphenyl)-2-(ethylamino) acetamide. The resulting mixture was heated to 100° C. for 10 min to afford the title product. The reaction mixture was purified using semi-preparative HPLC yielding pure and injectable N-(2,6-dimethylphenyl)-2-(ethyl(2-(fluoro-$^{18}$F)ethyl)amino)acetamide. (≥99.5% radiochemical purity). The isolated, non-decay corrected radiochemical yield typically ranged from 40-60%. The specific activity of N-(2,6-dimethylphenyl)-2-(ethyl(2-(fluoro-$^{18}$F)ethyl)amino)acetamide was determined using an analytical HPLC calibration curve. At the time of injection, specific activity was 4.9±3.5 mCi/nmol. Analytical HPLC: $R_f$=4.65 min. Semipreparative HPLC: 17-18 min.

Example 3. Ex Vivo Autoradiography of Rat Myocardium

Heart sections (20 m thickness) were prepared using a −20° C. cryostat and thaw-mounted onto gelatin-coated slides. The slides were stored at −20° C. until the day of the experiment. Sections were then incubated at room temperature in 50 mL baths containing either 10 mM Tris-HCl or 10 mM Tris-HCl and the indicated concentration of lidocaine or N-(2,6-dimethylphenyl)-2-(ethyl(2-fluoroethyl)amino)acetamide for 10 min. 100 Ci of N-(2,6-dimethylphenyl)-2-(ethyl(2-(fluoro-$^{18}$F)ethyl)amino)acetamide was added to each bath. Following 15 min incubation at room temperature, sections were dipped 3× in a fresh bath containing 10 mM Tris-HCl and subsequently washed for 1 min in an additional bath of 10 mM Tris-HCl. Slides were carefully wiped dry on absorbent towels, dried under vacuum for 30 min and exposed for 1 h to a multisensitive phosphorscreen developed using a Cyclone Plus phosphorimager (both from PerkinElmer) and the resulting parent image was evaluated using ImageJ software (NIH). Individual images of sections were cropped using ImageJ with no additional adjustment to color levels/thresholds. The experimental setup was designed such that both baseline and competition experiments contained the same amount of radioactivity and were imaged on the same screen. For variation of incubation times, the washing time was held constant at 1 min. For variation of washing times, the incubation was held constant at 15 min.

Using ex vivo imaging by means of F-18 autoradiography, the extent of N-(2,6-dimethylphenyl)-2-(ethyl (2-(fluoro-$^{18}$F)ethyl)amino)acetamide specific binding was determined in the rat myocardium and its association and dissociation time course were measured. FIG. 1A shows images of a healthy rat myocardial slices (20 μm) incubated with N-(2,6-dimethylphenyl)-2-(ethyl(2-(fluoro-$^{18}$F)ethyl) amino)acetamide (top) or N-(2,6-dimethylphenyl)-2-(ethyl (2-(fluoro-$^{18}$F)ethyl)amino)acetamide with excess N-(2,6-dimethylphenyl)-2-(ethyl(2-fluoroethyl)amino)acetamide (bottom) for self-competition. The upper image of FIG. 1A shows a strong and homogeneous signal across the entire myocardium of the right and left ventricle (RV & LV). The competition experiment shown in the lower image demonstrated that nearly all of the observed signal was saturable and specific binding ($B_S$) accounted for ~70% of overall binding, as shown in FIG. 1B. A comparison between lidocaine and N-(2,6-dimethylphenyl)-2-(ethyl(2-fluoroethyl)amino)acetamide as competition ligands, as shown in FIG. 1B, revealed that N-(2,6-dimethylphenyl)-2-(ethyl(2-fluoroethyl)amino)acetamide provided the same level of $B_{NS}$ as lidocaine, which showed that the compounds are mutually exclusive for receptor sites in the myocardium. In addition, both saturating concentrations of lidocaine and N-(2,6-dimethylphenyl)-2-(ethyl(2-fluoroethyl)amino)acetamide can be used to determine $B_S$. Using the DeBlasi considerations for determination of receptor numbers, $B_S$ directly correlates to $B_{max}$ and was used for quantitative comparison of channel populations (see e.g., DeBlasi et al, *Trends Pharmacol. Sci.* 1989, 10:227-229).

Figure 1C:
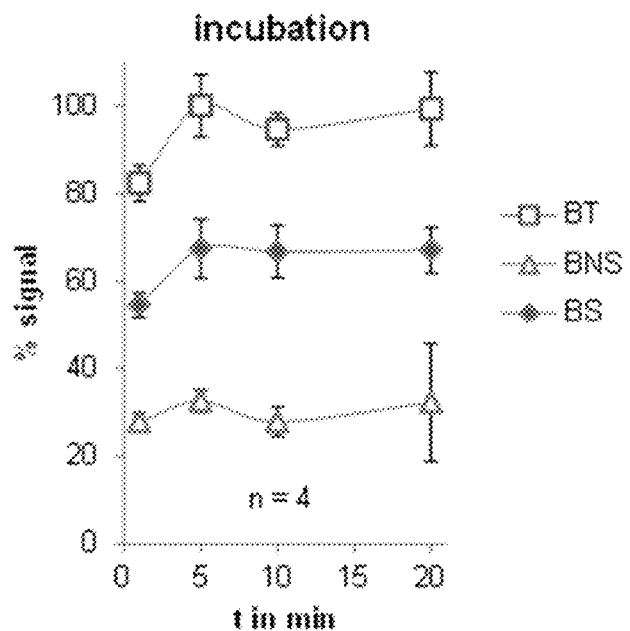
FIG. 1C shows incubation times of 1, 5, 10 and 20 min tested to investigate equilibrium conditions. After 5 min of incubation with N-(2,6-dimethylphenyl)-2-(ethyl(2-(fluoro-$^{18}$F)ethyl)amino)acetamide, specific binding ($B_S$) reached a constant level ($B_T$=total binding; $B_{NS}$=nonspecific binding).
Figure 1D:
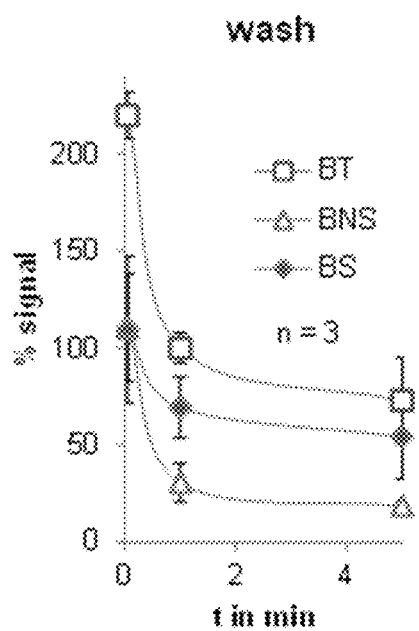
FIG. 1D shows washing times of 3 sec, 1 min, and 5 min tested to show signal to background conditions and the dissociation time course. Wash times of only 1 min were sufficient to reduce non-specific binding to a constant level (error bars represent one standard deviation; $B_S$=specific binding; $B_T$=total binding; $B_{NS}$=nonspecific binding).
Figure 1E:
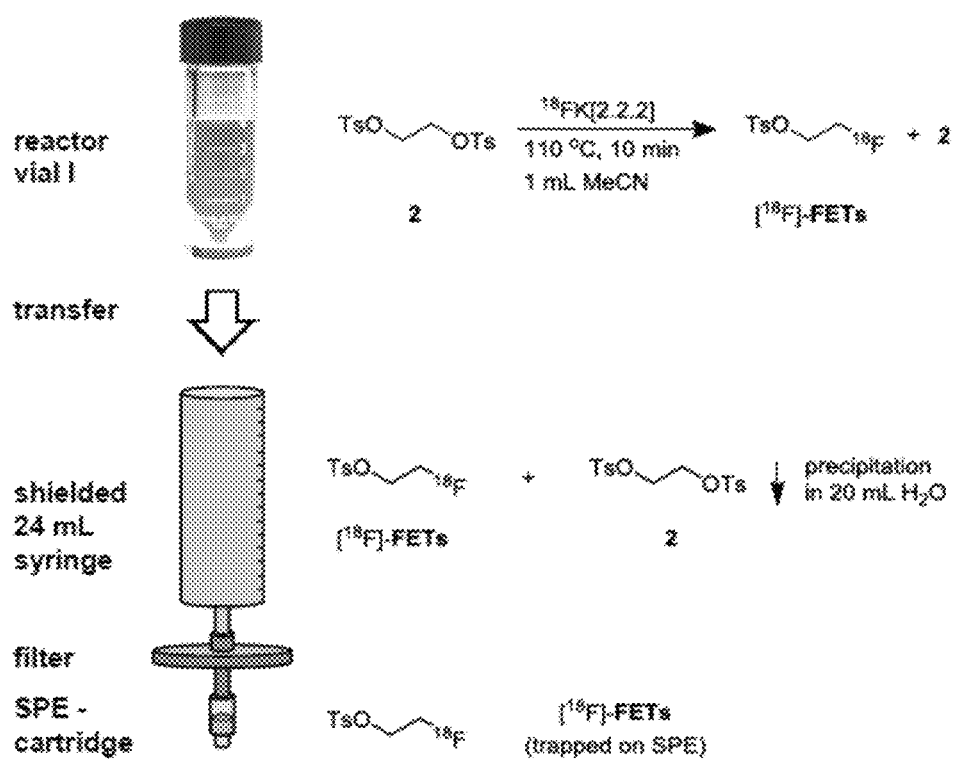
FIG. 1E shows the synthesis of [$^{18}$F]-fluoroethyltosylate ([$^{18}$F]FETs) via reaction of $^{18}$FK[2.2.2] with ethane-1,2-diyl bis(4-methylbenzenesulfonate). The [$^{18}$F]-fluoroethyltosylate was isolated from the remaining ethane-1,2-diyl bis(4-methylbenzenesulfonate) via precipitation of the ethane-1,2-diyl bis(4-methylbenzenesulfonate) upon addition of $H_2O$ and subsequent filtration.

To ensure that the protocol represented binding equilibrium conditions, incubation times were varied, as shown in FIG. 1C, and it was determined that the specific binding ($B_S$) reached a constant level after a 5 min incubation. Similar to rapid kinetics towards binding equilibrium, the time-course of wash-out was fast, as shown in FIG. 1D, with a 50% reduction of total binding after 1 min. The fast time course of association and dissociation observed in N-(2,6-dimethylphenyl)-2-(ethyl(2-(fluoro-$^{18}$F)ethyl)amino)acetamide autoradiography matches the instant antiarrhythmic effect of a lidocaine infusion, which quickly ceases after the infusion is stopped (see e.g., Collinsworth et al, *Circulation,* 1974, 50:1217-1230).

Example 4. Rodent PET-CT or PET Data Acquisition and Processing

Male Sprague-Dawley rats (400-500 g) were anesthetized with inhalational isoflurane (Forane) (3% in a carrier of 1.5-2 L/min medical oxygen for induction and 2% isoflurane for maintenance of anesthesia during the scan). Lateral tail vein catheters were placed for intravenous (i.v.) injection of the compounds. Two rats were arranged head-to-head in a Triumph Trimodality PET/CT/SPECT scanner (Gamma Medica, Northridge, Calif.) or a MicroPET P4 scanner. Rats were injected with lidocaine dissolved in saline or pure saline 5 minutes before the start of PET acquisition and injection of N-(2,6-dimethylphenyl)-2-(ethyl(2-(fluoro-$^{18}$F)ethyl)amino)acetamide. Dynamic PET acquisition was performed over 45 min and was followed by computed tomography (CT) for anatomic coregistration and attenuation correction. PET data were reconstructed using a 3D-MLEM method resulting in a full width at half-maximum (fwhm) resolution of 1 mm. Reconstructed images were exported from the scanner in DICOM format along with an anatomic CT for rodent studies. These files were imported to AMIDE and Gaussian filtered (kernel size=15, fwhm=1.5 mm). Regions of interest (ROIs) were drawn manually at the lung and myocardium guided by high-resolution CT structural images and summed PET data. Time-activity-curves (TACs) were exported in terms of decay corrected activity per unit volume at specified time points with gradually increasing intervals.

The in vivo cardiac mPET imaging experiments in healthy rats were used to determine the extent of specific binding and the signal to background ratio in the living heart for comparison to autoradiography, as shown in FIGS. 2A-2E.

Figure 2A:
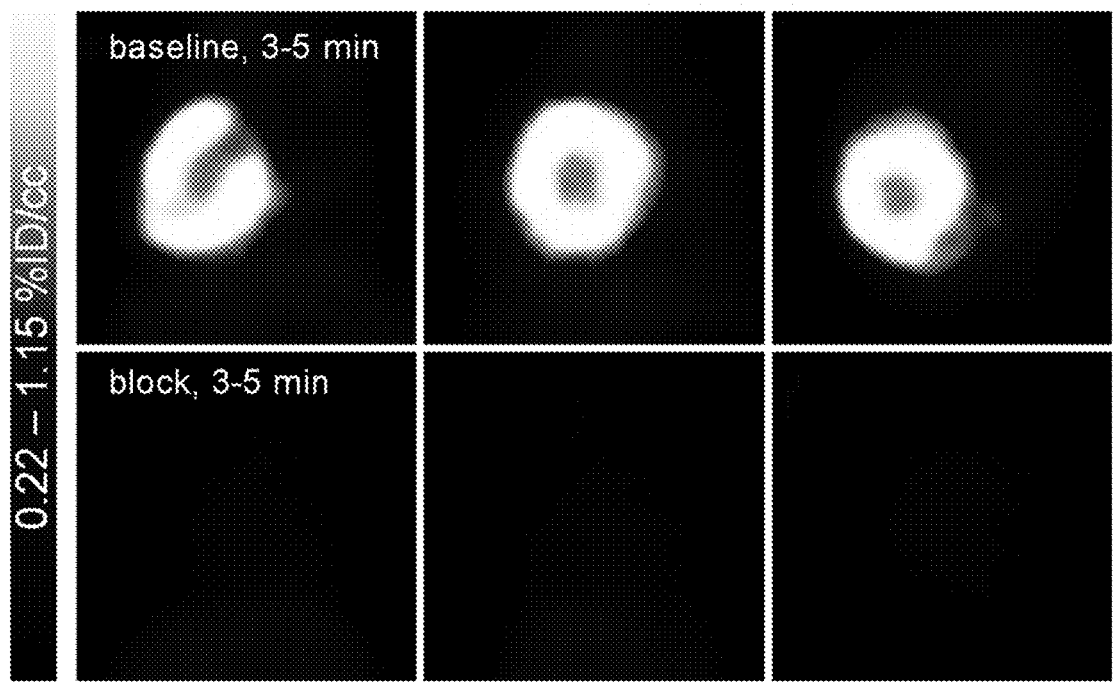
FIG. 2A shows summed images (3-5 min) of rat myocardium after an intravenous (i.v.) bolus injection of 750 μCi N-(2,6-dimethylphenyl)-2-(ethyl(2-(fluoro-$^{18}$F)ethyl)amino)acetamide (top) or a 5 mg/kg dose (i.v.) of lidocaine dissolved in saline five minutes before 1036 μCi N-(2,6-dimethylphenyl)-2-(ethyl(2-(fluoro-$^{18}$F)ethyl)amino)acetamide (bottom) (baseline animal was injected with an equivalent volume of saline). The images show coronal, sagittal and transverse views of the rat thorax.
Figure 2B:
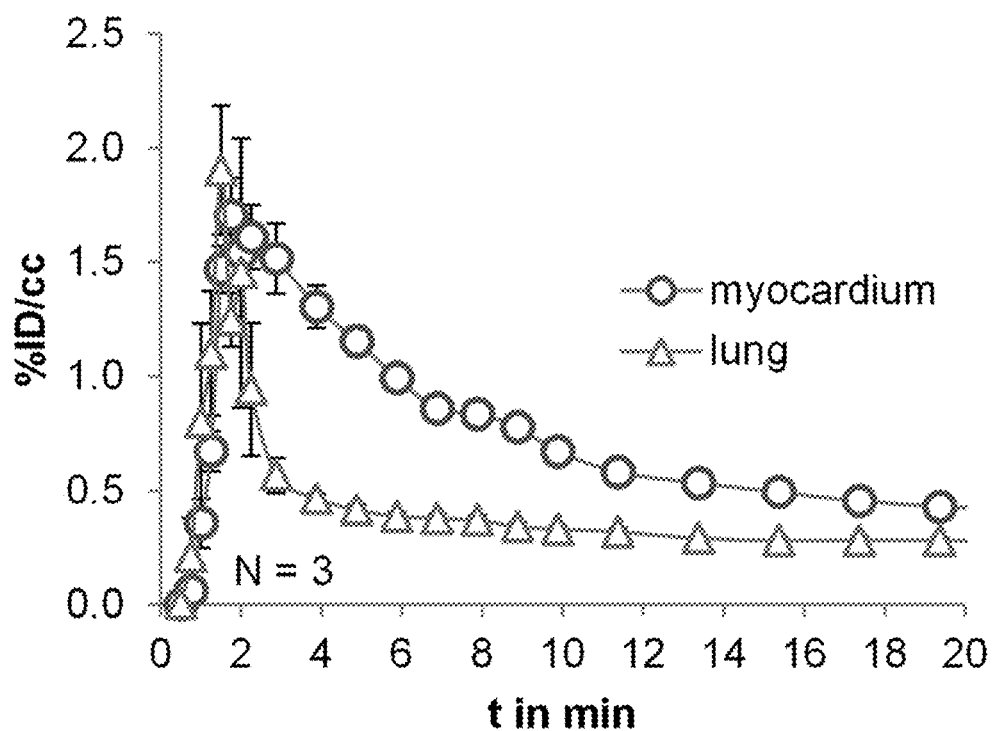
FIG. 2B shows time-activity-curves (TACs) of rat myocardium and lung (N=3, error bars represent one standard deviation).

Single bolus injections of N-(2,6-dimethylphenyl)-2-(ethyl(2-(fluoro-$^{18}$F)ethyl)amino)acetamide (i.e., radiocaine) provided a full representation of the rat myocardium from coronal, sagittal and transverse views, as shown in FIG. 2A. Despite the movement from heart contraction and breathing, the non-motion-corrected images provided a clear view of the left ventricle; horseshoe-shaped in the coronal view or circular in sagittal- and transverse views. As shown in FIG. 2B, the myocardial baseline signal showed up to 2% ID/cc and the time-course of radiotracer binding was fast and correlated with the ex vivo experiments described herein. A comparison of the myocardium to the lung was used to assess clearance of the radiolabeled compound from the blood pool and signal to background ratio, as shown in FIG. 2B.

Figure 2C:
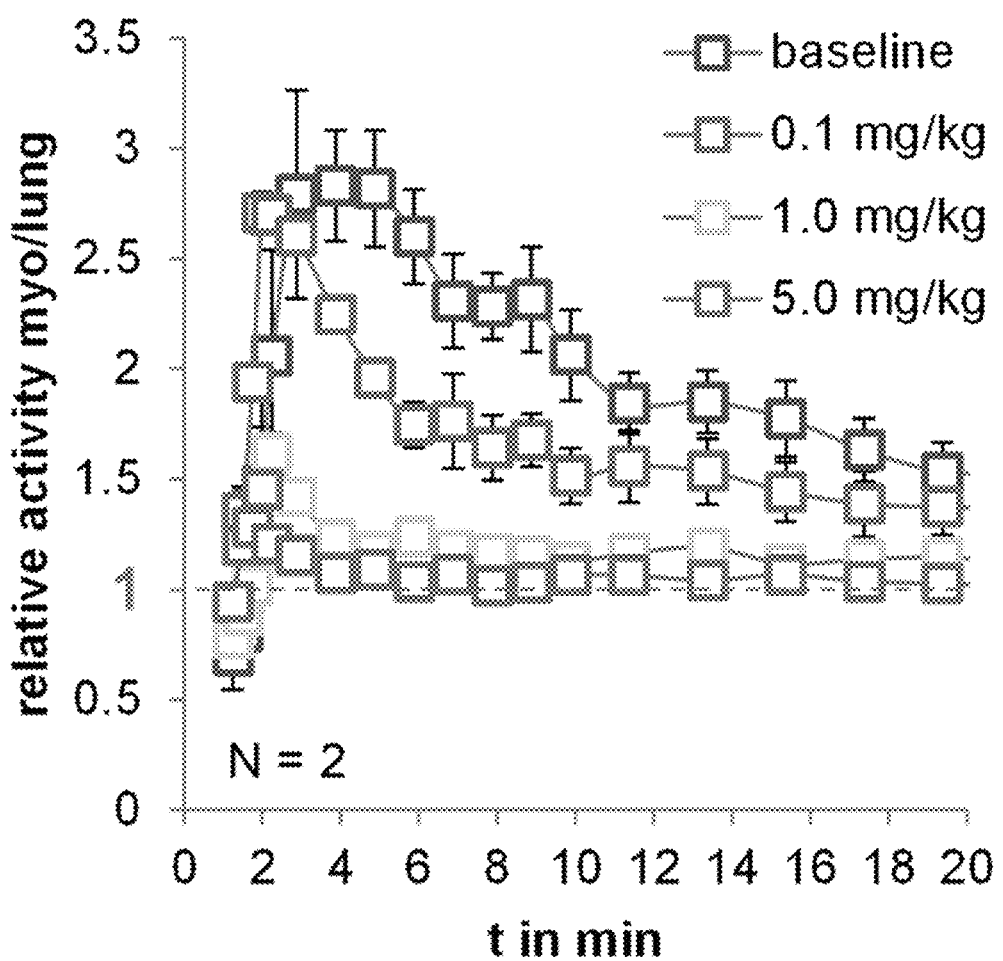
FIG. 2C shows ratio of myocardium to lung over time and as a function of drug occupancy. Doses of 0.1 mg/kg, 1.0 mg/kg, and 5.0 mg/kg lidocaine, or an equivalent volume of saline were injected (i.v.) 5 min before injection of N-(2,6-dimethylphenyl)-2-(ethyl(2-(fluoro-$^{18}$F)ethyl)amino)acetamide (N=2 for each dose, error bars represent one standard deviation).

Clearance from the blood pool was very fast, revealing the rapid myocardial signal only 3 min after bolus injection. To interrogate the specificity of the signal, increasing concentrations of lidocaine were administered intravenously 5 minutes prior to injection of the radiolabeled compound, as shown in FIG. 2C, to pre-occupy potential binding sites. The ratio of myocardial to lung signal was used as a measurement to assess the signal to background ratio as a function of drug occupancy. Compared to vehicle injection, signal reduction was observed starting at doses of 0.1 mg/kg lidocaine. The lower panel of FIG. 2A shows complete block of the myocardial radiocaine signal, which is represented by a signal to background ratio of 1 for a 5.0 mg/kg lidocaine dose, shown in FIG. 2C. The myocardial radiocaine signal was fully saturable and the extent of specific binding was even higher for the in vivo mPET rat experiments than the ex vivo autoradiography experiments described in Example 3.

Figure 2D:
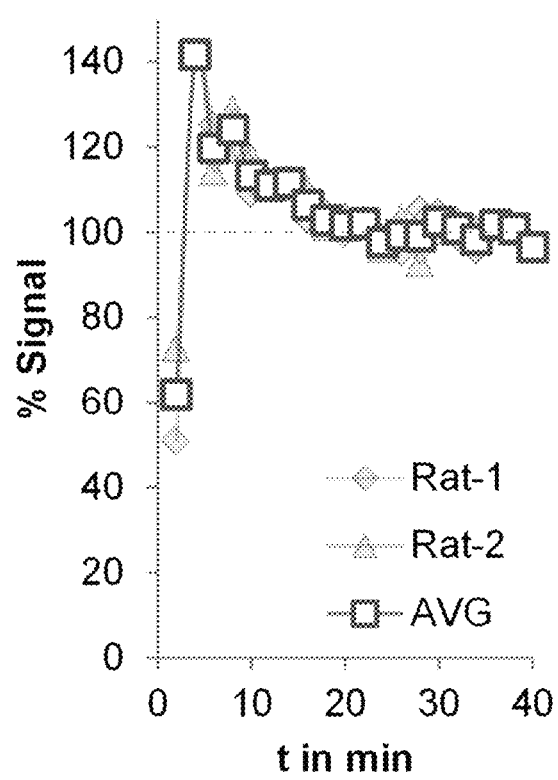
FIG. 2D shows a representative bolus+infusion paradigm. N-(2,6-dimethylphenyl)-2-(ethyl(2-(fluoro-$^{18}$F)ethyl)amino)acetamide was injected (i.v.) followed by continuous syringe-pump infusion for 40 min (rate=1 mL/hour). The signal represents the ratio of myocardium over lung and was normalized to the plateau after 20 min.
Figure 2E:
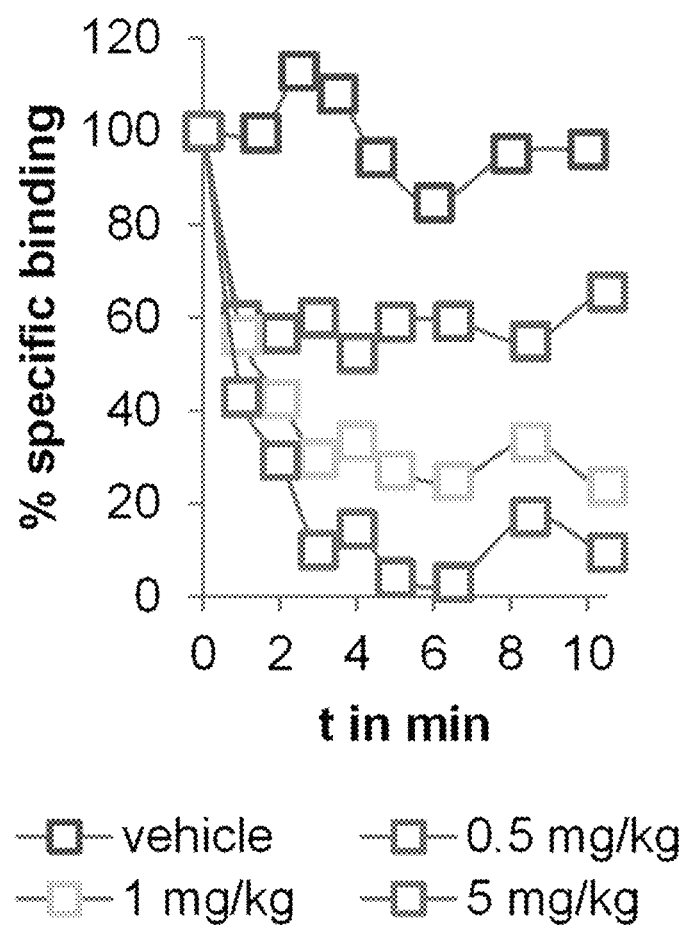
FIG. 2E shows a representative bolus+infusion paradigm with i.v. lidocaine injection during a dynamic PET scan with continuous radiotracer infusion (1 mL/hour). Using an additional i.v. line, the vehicle or increasing concentrations of lidocaine (0.5-5 mg/kg) were injected. Specific binding was calculated as the myocardium/lung ratio at the TAC-plateau minus the same ratio after injection of a 5.0 mg/kg lidocaine dose.

Next, bolus-infusion experiments were performed to investigate the radiocaine signal at equilibrium conditions and apply lidocaine challenges during the dynamic scan, as shown in FIG. 2D. Applying an intravenous bolus of ~150 µCi N-(2,6-dimethylphenyl)-2-(ethyl(2-(fluoro-$^{18}$F)ethyl)amino)acetamide followed by a constant infusion of ~300 µCi through the same vein over the course of 60 min provided a stable baseline signal after 20 min. Injection of vehicle through an additional i.v. line led to no change in signal, as shown in FIG. 2E. However, lidocaine injections reduced the signal in a dose-dependent manner. A complete reduction of the radiolabeled compound signal to background level was achieved with 5 mg/kg lidocaine, which correlated to the pre-block experimental data, as shown in FIG. 2C. The in-scan challenges allowed for an estimation of the in vivo $IC_{50}$ of lidocaine at the myocardium of ~0.7 mg/kg. Assuming a blood volume of 30 mL (500 mg rat) following the general equation BV=0.06×BW+0.77 (see e.g., Lee et al, *J. Nucl. Med.* 1985, 26:72-76) this value corresponds to a 40 µM concentration, which is in the expected range for lidocaine (see e.g., Hesse et al, *Cardiovasc. Res.* 2007, 75:498-509).

In addition, the time course of the reduction in N-(2,6-dimethylphenyl)-2-(ethyl(2-(fluoro-$^{18}$F)ethyl)amino)acetamide signal allowed for an estimation of the residence time ($t_{1/2}^{-1}$) of the radiotracer at ~1 min$^{-1}$. It was noted that the plateau of the full block with a 5 mg/kg lidocaine dose was reached only 3 minutes after the pharmacological dose, which is the same time that the N-(2,6-dimethylphenyl)-2-(ethyl(2-(fluoro-$^{18}$F)ethyl)amino)acetamide bolus needs to reach its peak signal, as shown in FIG. 2C. This indicates that the radiolabeled compound and nd lidocaine have very similar binding kinetics.

Example 5. PET/MR Imaging of Non-Human Primates

Two female baboons (Papio anubis, weight=15.2±1.6 kg) were deprived of food for 12 h prior to the study. Anesthesia was induced with intramuscular ketamine (10 mg/kg) and xylazine (0.5 mg/kg). After endotracheal intubation, the baboons were catheterized antecubitally for injection of the radiolabeled compound. Anesthesia was maintained using isoflurane (1-1.5%, 100% oxygen, 1 L/min) during the scan, and ketamine/xylazine effects were reversed with yobine (0.11 mg/kg, i.m.) before image acquisition. Vital signs, including heart rate, respiration rate, blood pressure, $O_2$ saturation, and end tidal $CO_2$, were monitored continuously and recorded every 15 min. Simultaneous PET/MR data were acquired using a Siemens Biograph mMR system (Siemens Healthcare, Erlangen, Germany). Each animal underwent a baseline and a blocking scan on two separate days. MR body imaging was performed with real-time respiratory bellow gating and using the body matrix coil and the built-in spine coil as the receiving coil elements. High-resolution anatomical T1-weighted, dual echo, gradient echo sequence was acquired with the following parameters: TR=194 ms, TE1/TE2=1.23/2.46 ms, matrix size 256×256, FOV=35 cm, phase FOV 65.6% (in-plane resolution=1.4 mm), 4 mm slice thickness, and 80 slices. For the purpose of MR-based attenuation correction of the PET data, a T1-weighted, 2-point Dixon 3D volumetric interpolated breath-hold examination (VIBE) scan was obtained. PET data were obtained using a single-bed position with an axial field of view of 25.8 cm, and a transverse field of view of 59.4 cm. PET data were acquired dynamically for 60 min (bolus injection of N-(2,6-dimethylphenyl)-2-(ethyl(2-(fluoro-$^{18}$F)ethyl)amino)acetamide) or 90 min (bolus/infusion of N-(2,6-dimethylphenyl)-2-(ethyl(2-(fluoro-$^{18}$F)ethyl)amino)acetamide) after intravenous administration of N-(2,6-dimethylphenyl)-2-(ethyl(2-(fluoro-$^{18}$F)ethyl)amino)acetamide (5.0±0.2 mCi bolus or 4 mCi bolus+4 mCi infusion). PET data were stored in list mode, and reconstruction was performed using a 3D-OSEM method with detector efficiency, decay, dead time, attenuation, and scatter corrections applied. ROIs of the left myocardium and the ventricle were manually delineated from the T1-weighted anatomical image as well as summed PET-images using AMIDE to plot time-activity curves of the myocardium and cardiac blood pool. Standard uptake unit (SUV) was calculated as the mean radioactivity per injected dose per weight.

Figure 3A:
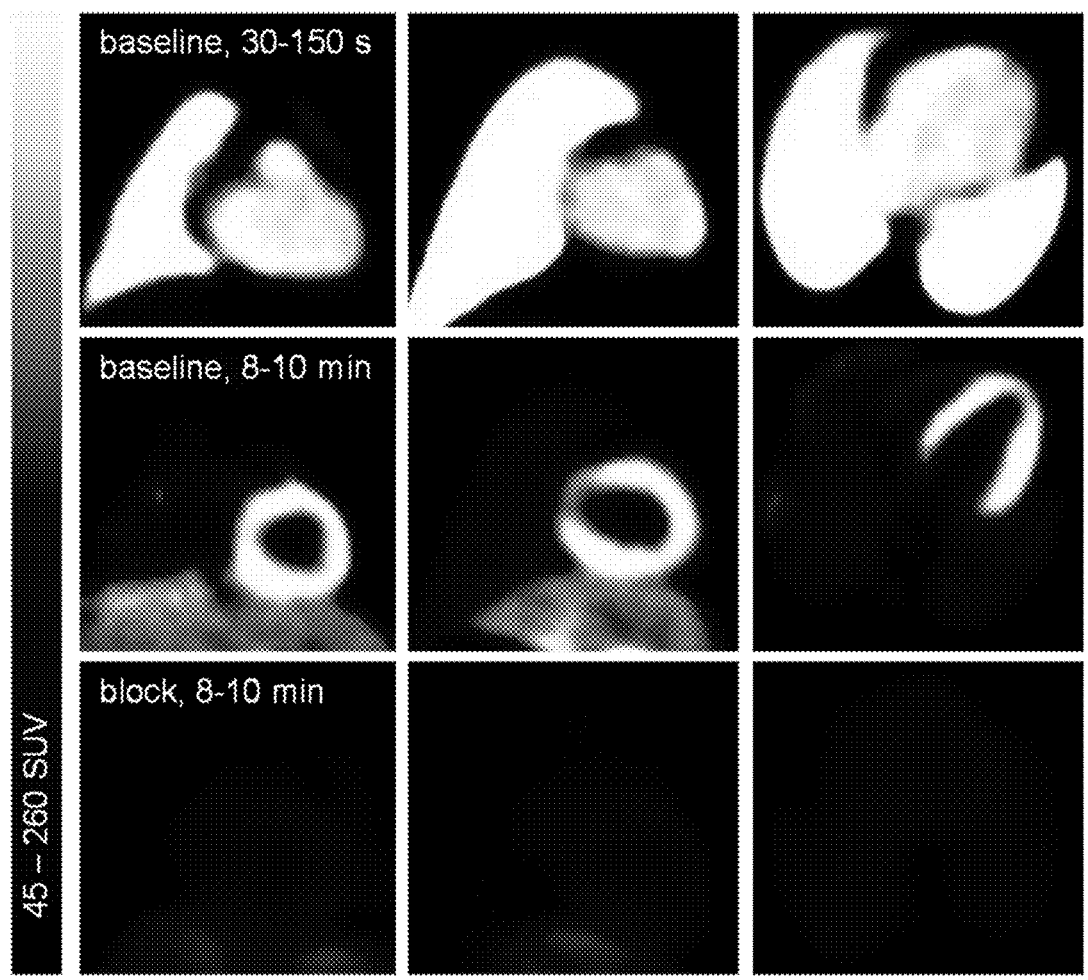
FIG. 3A shows thoracic PET-images of a baboon injected with 5.08 mCi N-(2,6-dimethylphenyl)-2-(ethyl(2-(fluoro-$^{18}$F)ethyl)amino)acetamide. Upper panel shows summed images (30-150 seconds) from coronal, sagittal and transverse view with blood-filled heart and lungs. The middle panel shows the same scan as the upper panel summed from 8-10 min with a clear myocardial signal. The lower panel shows the same animal in a N-(2,6-dimethylphenyl)-2-(ethyl(2-(fluoro-$^{18}$F)ethyl)amino)acetamide scan and treated with 5 mg/kg (i.v.) lidocaine 5 minutes prior to injection of the radiolabeled compound.
Figure 3B:
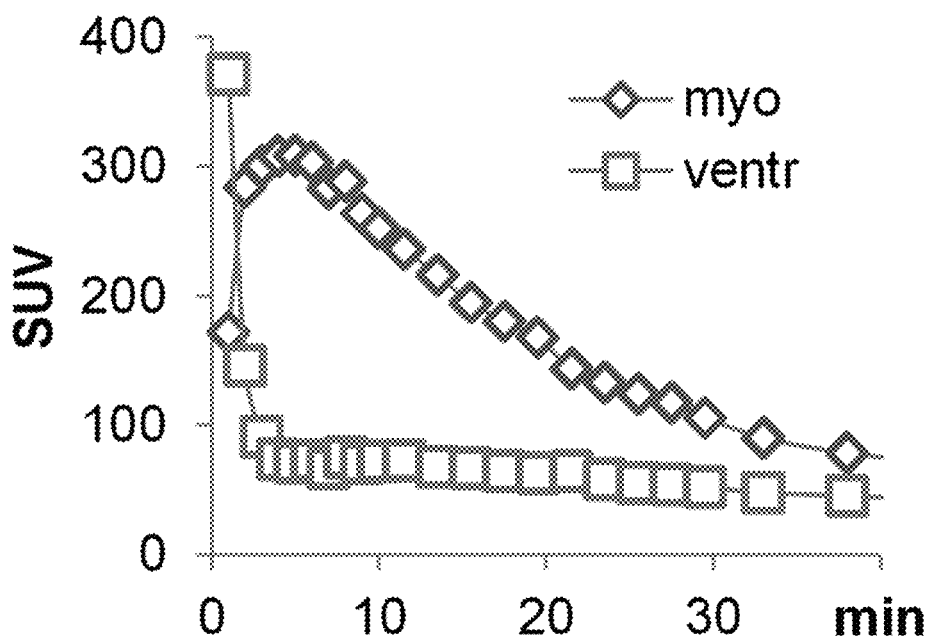
FIG. 3B shows TACs of the myocardium and ventricle of the baboon shown in the upper panel of FIG. 3A. The ventricle was used as an internal reference for measuring the N-(2,6-dimethylphenyl)-2-(ethyl(2-(fluoro-$^{18}$F)ethyl)amino)acetamide blood signal.
Figure 3C:
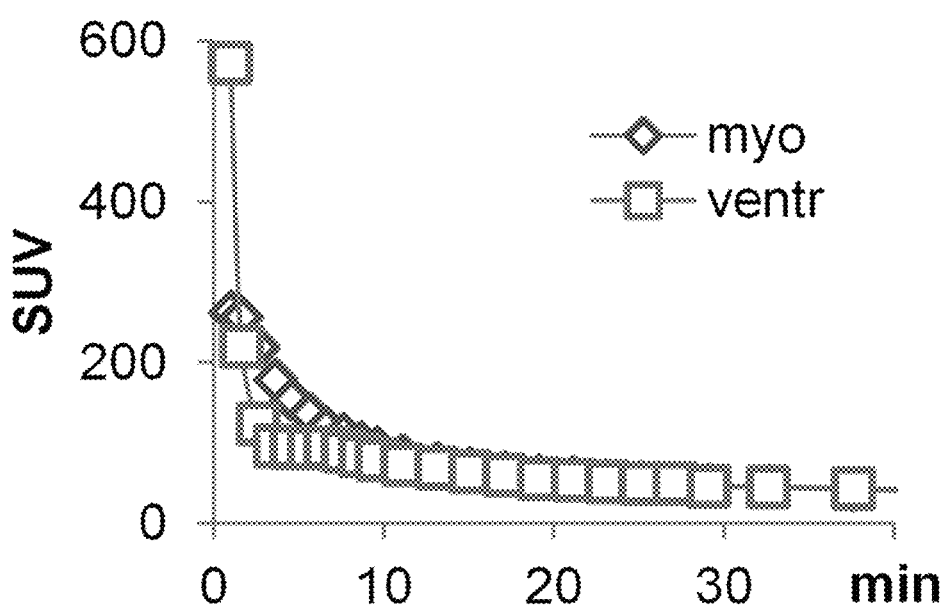
FIG. 3C shows TACs of the baboon shown in the lower panel of FIG. 3A. The competition ligand lidocaine, injected 5 minutes prior to N-(2,6-dimethylphenyl)-2-(ethyl(2-(fluoro-$^{18}$F)ethyl)amino)acetamide suppressed the myocardial signal to background levels.
Figure 3D:
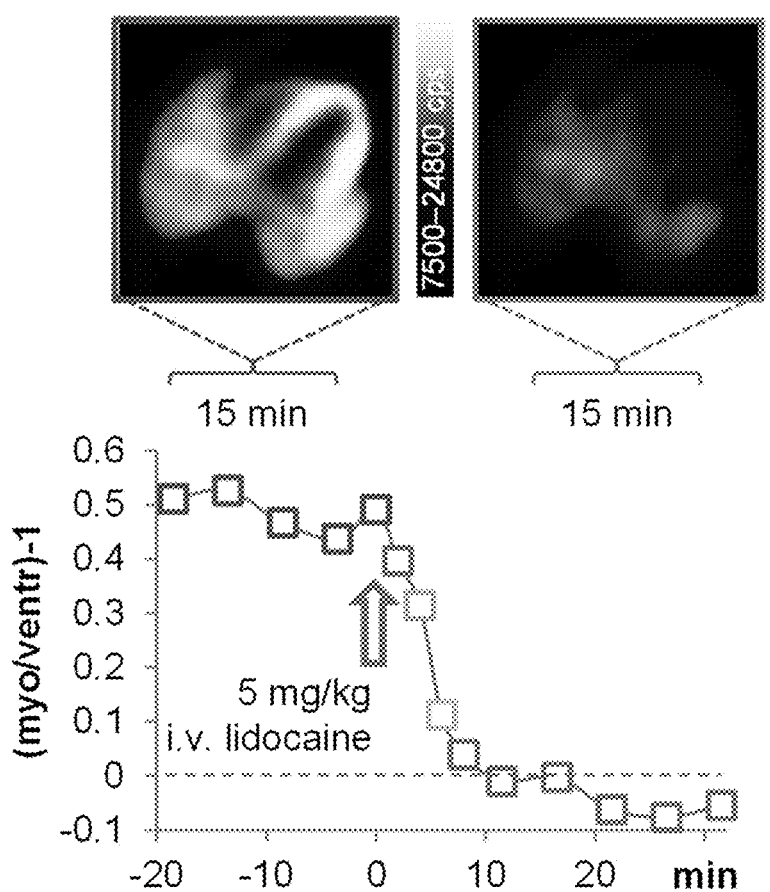
FIG. 3D shows images of a baboon treated with a bolus+infusion paradigm, followed by an in-scan lidocaine challenge. A dose of 5.0 mg/kg lidocaine was injected after the myocardial signal had reached a plateau. 10 min after administration of the lidocaine, the myocardial signal was reduced to background levels.

The extent of signal specificity and background clearance was measured and is shown in FIG. 3A-3C. Single bolus injection of the radiolabeled compound in a healthy baboon provided a full representation of the myocardium, as shown in FIGS. 3A-3B. At early time points (30-150 s), the thoracic PET scan showed the blood-filled heart and lungs. After 2-3 min, the blood background cleared, as shown in FIG. 2B, and the left myocardium appeared as a strong signal with up to 300 SUV. When compared to the in vivo rodent experiments described in Example 4, the larger organ of the baboon also provided resolution of a signal within the right myocardium, however with much lower intensity, which would be expected for the smaller, weaker muscle. Administering a 5 mg/kg dose of lidocaine prior to injection of the radiolabeled compound blocked the myocardial signal, as shown in FIG. 3A, lower panel, and FIG. 3C. It was concluded that the N-(2,6-dimethylphenyl)-2-(ethyl(2-(fluoro-$^{18}$F)ethyl)amino)acetamide signal at the myocardium of non-human primates was specific. The evident difference between the right and left myocardial signal in the same animal was a useful indicator for the expected change in radiolabeled compound signal that may be observed in cardiomyopathies.

The specific binding was confirmed in a second baboon, and was measured using a bolus+infusion paradigm. The animal was injected with a bolus of 4 mCi radiocaine, followed by continuous administration of 4 mCi radiocaine over 90 min scan. A dose of 5 mg/kg lidocaine was administered (through a second i.v. line) after equilibrium conditions were reached. Within 10 minutes, the myocardial signal had reached the background level of the ventricle, with an estimated residence time of 5 min$^{-1}$. The overall time-course of binding in both bolus and bolus+infusion experiments was longer in baboons than in rats, which was expected for the high order species. However, scan-times of only 20-30 min were sufficient to capture the majority binding kinetics which is useful for human imaging, in particular with the ventricle or the lungs as an internal quantitative reference.

Example 6. Ex Vivo Autoradiography of Human Heart Tissue

Figure 4A:
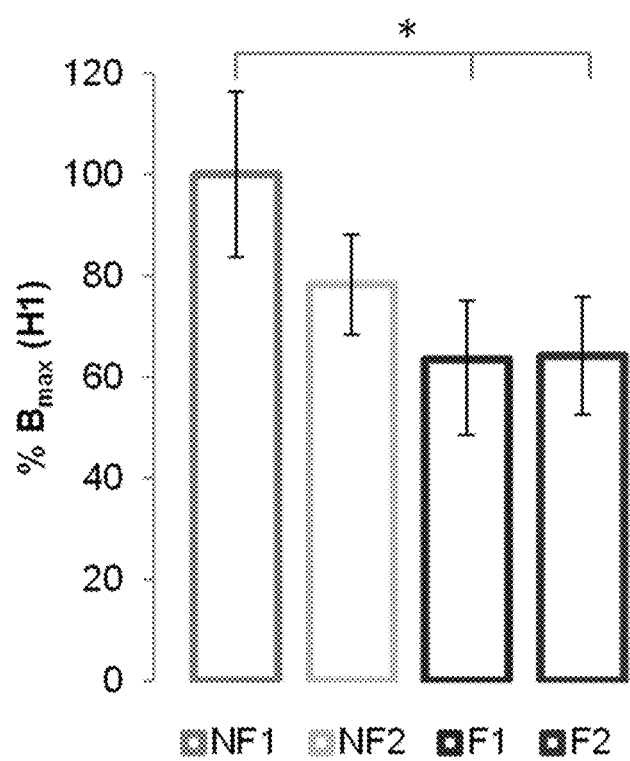
FIG. 4A shows a comparison of specific N-(2,6-dimethylphenyl)-2-(ethyl(2-(fluoro-$^{18}$F)ethyl)amino)acetamide signal relative to heart tissues samples from non-failing group NF1 determined by autoradiography at equilibrium conditions with 500 μM lidocaine as blocking agent (N=5, n≥13, significance * is defined by p<0.05 as determined by student t-test).
Figure 4B:
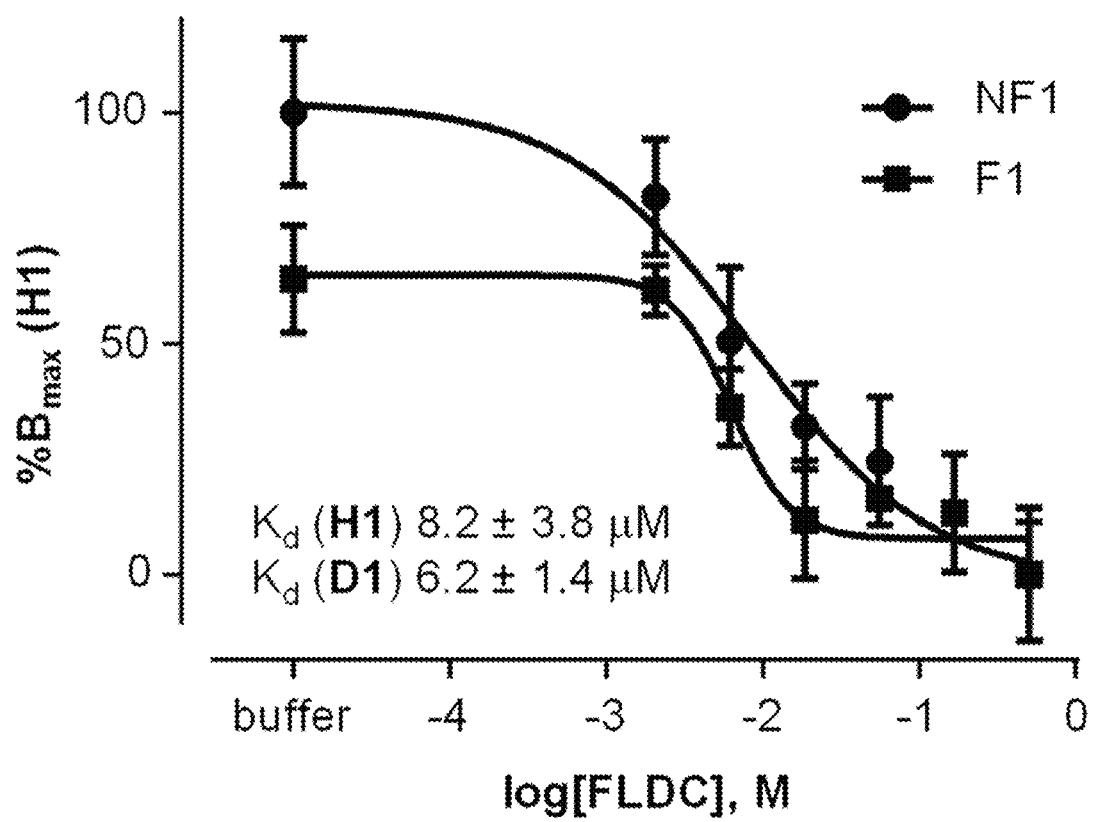
FIG. 4B shows dose-response experiments with increasing concentrations of N-(2,6-dimethylphenyl)-2-(ethyl(2-fluoroethyl)amino)acetamide. Using self-displacement, the $IC_{50}$-value generated with this assay equaled the $K_d$-value (error bars represent one standard deviation).

To detect changes is SCN5A density in healthy and diseased human left ventricular tissue samples, the autoradiography conditions described in Example 1 were used (15 min incubation, 1 min wash) and lidocaine was used as the competition ligand at 500 μM concentration. Non-failing human donor heart samples were compared to explanted tissue from patients who had suffered from heart failure due to idiopathic dilated cardiomyopathy (DCM) and required cardiac transplantation, as shown in FIGS. 4A-4B (see e.g., Japp et al, *J. Am. Coll. Cardiol.* 2016, 67:2996-3010).

Tissue samples encompassed a moderately sized group of age and gender matched subjects, as shown in Table 1 (NF=non-failing, F=failing (idiopathic dilated cardiomyopathy)).

TABLE 1

| Summary of Subjects | | | |
|---|---|---|---|
| NF1 age (y) | F1 age (y) | NF2 age (y) | F2 age (y) |
| 37 | 41 | 54 | 51 |
| 40 | 43 | 56 | 59 |
| 46 | 45 | 60 | 62 |
| 47 | 45 | 60 | 63 |
| 53 | 46 | 65 | 65 |
| AVG 44.6 ± 6.3 | AVG 44.0 ± 2.0 | AVG 59.0 ± 4.2 | AVG 60.0 ± 5.5 |

A ~30% decrease of $B_{max}$ between NF1 and F1 was observed, as shown in FIG. 4A, which is the first time that cardiac sodium channel density has been linked to heart failure in humans. In addition, a trend was observed between the two healthy groups NF1 and NF2 as signal reduced with age.

To exclude that the reduced signal was the result of a decrease in affinity in diseased vs. healthy tissue and confirm a deficit in channel density, dose-response experiments were performing using N-(2,6-dimethylphenyl)-2-(ethyl(2-fluoroethyl)amino)acetamide as the competition ligand. Using the modified Cheng-Prusoff equation for self-inhibition, these measurements allowed for the determination of $K_d$-values for the groups NF1 and F1, as shown in FIG. 4B. It was found that on average there was no difference in $K_d$-values between the groups. A ~30% reduction in $B_{max}$ was observed. It was concluded from these data that the sodium channel density was reduced in tissue samples of DCM-failing myocardium compared to non-failing, age-matched tissue.

Other Embodiments

It is to be understood that while the invention has been described in conjunction with the detailed description thereof, the foregoing description is intended to illustrate and not limit the scope of the invention, which is defined by

What is claimed is:

1. A process of preparing a compound of Formula VIII:

(R³)ₙ—[phenyl]—NH—C(=O)—CH₂—N(R¹)—CH₂CH₂—F  (VIII)

or a salt thereof, comprising reacting a compound of Formula Ic:

(R³)ₙ—[phenyl]—NH—C(=O)—CH₂—NH(R¹)  (Ic)

with a compound of Formula IX:

F—CH₂CH₂—LG  (IX)

in the presence of a base, wherein:
LG is a leaving group;
$R^1$ is selected from the group consisting of H, $C_{1-6}$ alkyl, and $C_{1-6}$ haloalkyl;
each $R^3$ is independently selected from the group consisting of halo, $C_{1-6}$ alkyl, and $C_{1-6}$ haloalkyl; and
n is an integer from 0 to 5.

2. The process of claim 1, wherein the base is a carbonate base.

3. The process of claim 1, wherein the reacting is performed at a temperature of about 50° C. to about 150° C.

4. The process of claim 1, wherein about 1 to about 1.5 equivalents of the compound of Formula IX is used based on 1 equivalent of the compound of Formula Ic.

5. A process of preparing a compound of Formula X:

(R³)ₙ—[phenyl]—NH—C(=O)—CH₂—N(R¹)—CH₂CH₂—$^{18}$F  (X)

or a salt thereof, comprising reacting a compound of Formula Ic:

(R³)ₙ—[phenyl]—NH—C(=O)—CH₂—NH(R¹)  (Ic)

with a compound of Formula IXa:

$^{18}$F—CH₂CH₂—LG  (IXa)

wherein:
LG is a leaving group;
$R^1$ is selected from the group consisting of H, $C_{1-6}$ alkyl, and $C_{1-6}$ haloalkyl;
each $R^3$ is independently selected from the group consisting of halo, $C_{1-6}$ alkyl, and $C_{1-6}$ haloalkyl; and
n is an integer from 0 to 5.

6. The process of claim 5, wherein the reaction is performed at a temperature of about 50° C. to about 150° C.

7. The process of claim 5, wherein LG is a leaving group selected from the group consisting of tosylate, mesylate, and a halide.

8. The process of claim 5, wherein LG is a leaving group selected from the group consisting of tosylate, mesylate, and bromide.

9. The process of claim 5, wherein LG is a leaving group selected from the group consisting of tosylate and mesylate.

10. The process of claim 5, wherein LG is a tosylate group.

11. The process of claim 1, wherein the reaction is performed in a solvent selected from a polar aprotic solvent or a polar protic solvent.

12. The process of claim 11, wherein the solvent is selected from the group consisting of dimethylsulfoxide, dimethylformamide, and acetonitrile.

13. The process of claim 11, wherein the solvent is selected from the group consisting of dimethylformamide and acetonitrile.

14. A process of preparing a compound of the following formula:

[2,6-dimethylphenyl]—NH—C(=O)—CH₂—N(Et)—CH₂CH₂—$^{18}$F or a salt thereof, comprising reacting N-(2,6-dimethylphenyl)-2-(ethylamino)acetamide with 2-(fluoro-$^{18}$F)ethyl 4-methylbenzenesulfonate, wherein the reacting is performed in a polar aprotic solvent.

15. The process of claim 14, wherein the reaction is performed as a one-pot synthesis.

16. The process of claim 14, wherein the polar aprotic solvent is dimethylsulfoxide.

17. A process of preparing a compound of the following formula:

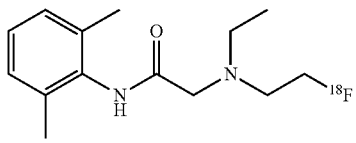 [SMILES: CCN(CC[18F])CC(=O)Nc1c(C)cccc1C]

or a salt thereof, comprising reacting N-(2,6-dimethylphenyl)-2-(ethylamino)acetamide with 1-bromo-2-(fluoro-$^{18}$F)ethane in the presence of NaI, wherein the reaction is performed in a polar aprotic solvent.

18. A process of preparing a compound of the following formula:

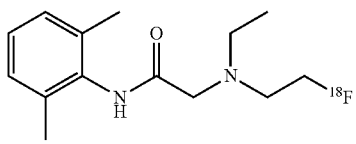 [SMILES: CCN(CC[18F])CC(=O)Nc1c(C)cccc1C]

or a salt thereof, comprising reacting N-(2,6-dimethylphenyl)-2-(ethylamino)acetamide with 1-(fluoro-$^{18}$F)-2-iodoethane, wherein the reaction is performed in a polar aprotic solvent.

19. A process of preparing a compound of the following formula:

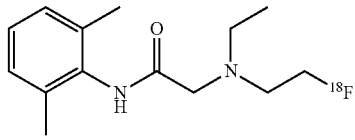 [SMILES: CCN(CC[18F])CC(=O)Nc1c(C)cccc1C]

or a salt thereof, comprising reacting N-(2,6-dimethylphenyl)-2-(ethylamino)acetamide with 1-(fluoro-$^{18}$F)-2-iodoethane, wherein the reaction is performed in a polar aprotic solvent.

20. A process of preparing a compound of the following formula:

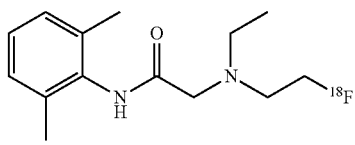 [SMILES: CCN(CC[18F])CC(=O)Nc1c(C)cccc1C]

or a salt thereof, comprising reacting N-(2,6-dimethylphenyl)-2-(ethylamino)acetamide with a mixture of 1-bromo-2-(fluoro-$^{18}$F)ethane and 1-(fluoro-$^{18}$F)-2-iodoethane, wherein the reaction is performed in a polar aprotic solvent.

* * * * *